(12) United States Patent
Yasuda et al.

(10) Patent No.: US 7,189,717 B2
(45) Date of Patent: Mar. 13, 2007

US007189717B2

(54) MEDICINAL COMPOSITIONS PROMOTING BOWEL MOVEMENT

(75) Inventors: Masahiro Yasuda, Ibaraki (JP); Hitoshi Harada, Ibaraki (JP); Shuhei Miyazawa, Ibaraki (JP); Seiichi Kobayashi, Belmont, MA (US); Kokichi Harada, Ibaraki (JP); Takayuki Hida, Ibaraki (JP); Hisashi Shibata, Ibaraki (JP); Nobuyuki Yasuda, Ibaraki (JP); Osamu Asano, Ibaraki (JP); Yoshihiko Kotake, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 371 days.

(21) Appl. No.: 10/257,091

(22) PCT Filed: Apr. 26, 2001

(86) PCT No.: PCT/JP01/03643

§ 371 (c)(1),
(2), (4) Date: Oct. 9, 2002

(87) PCT Pub. No.: WO01/80893

PCT Pub. Date: Nov. 1, 2001

(65) Prior Publication Data

US 2003/0171383 A1    Sep. 11, 2003

(30) Foreign Application Priority Data

Apr. 26, 2000 (JP) ............................. 2000-126489
Jul. 21, 2000 (JP) ............................. 2000-220124

(51) Int. Cl.
*A61K 31/506* (2006.01)

(52) U.S. Cl. .................. 514/235.8; 514/256; 514/275; 544/122; 544/333

(58) Field of Classification Search ................ 514/256, 514/275, 235.8; 544/122, 333
See application file for complete search history.

(56) References Cited

U.S. PATENT DOCUMENTS

| 4,725,600 | A | | 2/1988 | Takaya et al. |
| 5,763,448 | A | * | 6/1998 | Carling et al. .............. 514/274 |
| 6,096,753 | A | | 8/2000 | Spohr et al. |
| 6,495,528 | B1 | | 12/2002 | Allen et al. |

FOREIGN PATENT DOCUMENTS

| CN | 1088053 | | 6/1994 |
| EP | 0 216 247 | A2 | 4/1987 |
| EP | 1136482 | A1 | 9/2001 |
| EP | 1136486 | A1 | 9/2001 |
| HU | 0103025 | | 12/2001 |
| JP | 3-173889 | A | 7/1991 |
| JP | 4271770 | A | 9/1992 |
| JP | 6-211669 | A | 8/1994 |
| JP | 11-263789 | A | 9/1999 |
| WO | 94/16702 | A1 | 8/1994 |
| WO | 97/33883 | A1 | 9/1997 |
| WO | WO 97/33883 | * | 9/1997 |
| WO | WO 98/24780 | A2 | 6/1998 |
| WO | WO 98/24782 | A2 | 6/1998 |
| WO | 99/35147 | A1 | 7/1999 |
| WO | WO99/62518 | A1 | 12/1999 |
| WO | WO99/64418 | A1 | 12/1999 |
| WO | WO-00/18758 | A1 | 4/2000 |
| WO | WO00/24742 | A1 | 5/2000 |
| WO | WO-01/70727 | A1 | 9/2001 |
| WO | WO 01/02400 | A1 | 11/2001 |
| WO | WO 01/80893 | A1 | 11/2001 |

OTHER PUBLICATIONS

Yong-Chul Kim et al.; J. Med. Chem. 2000, No. 43, pp. 1165-1172.
Maarten de Zwart et al.; Drug Development Research, No. 48, pp. 95-103, 1999.
Igor Feoktistov et al.; J. Clin. Invest., vol. 96, pp. 1979-1986, 1995.
Robert F. Bruns et al.; Molecular Pharmacology, vol. 29, pp. 331-346, 1986.
W. Wan et al.; Journal of Neurochemistry, vol. 55, No. 5, pp. 1763-1771, 1990.
Dietrich van Calker et al.; Journal of Neurochemistry, vol. 33, pp. 999-1003, 1979.
Duncan R. Hannah et al.; Bioorganic & Medicinal Chemistry, vol. 8, No. 4, pp. 739-750, 2000.
Chemical Abstracts, vol. 77, Abstract No. 34471j, 1972. pp. 518.
Kadowaki et al., British Journal of Pharmacology, vol. 129, pp. 871-876 (2000).
Nitahara et al., Neuroscience, vol. 67, No. 1, pp. 159-168 (1995).
Peachey et al., Naunyn-Schmiedeberg's Arch Pharmacol., vol. 359, pp. 140-146 (1999).
Tomaru et al., European Journal of Pharmacology, vol. 264, pp. 91-94 (1994).
Christofi et al., Gastroenterology, vol. 104, pp. 1420-1429 (1993).
Suzuki et al., Jpn. J. Pharmacol., vol. 68, pp. 119-123 (1995).
Dixon et al., British Journal of Pharmacology, vol. 118, pp. 1461-1468 (1996).
Klauser et al., Pharmacology, vol. 47, Supp. 1, pp. 256-260, (1993).
Skulnick et al., J. Med. Chem. vol. 28, pp. 1864-1869, (1985).

* cited by examiner

*Primary Examiner*—Shaojia A. Jinag
*Assistant Examiner*—Ganapathy Krishnan
(74) *Attorney, Agent, or Firm*—Birch, Stewart, Kolasch & Birch, LLP

(57) ABSTRACT

The present invention provides a medicament having a gentle but strong defecation-promoting action without causing diarrhea. That is, it provides a defecation-promoting agent comprising a compound having an adenosine $A_2$ receptor antagonism, preferably an adenosine $A_{2b}$ receptor antagonism, or a salt thereof.

6 Claims, No Drawings

MEDICINAL COMPOSITIONS PROMOTING BOWEL MOVEMENT

This application is the national phase under 35 U.S.C. § 371 of PCT International Application No. PCT/JP01/03643 which has an International filing date of Apr. 26, 2001, which designated the United States of America.

TECHNICAL FIELD

The present invention relates to a novel pharmaceutical composition promoting defecation, and to a novel pyrimidine compound or a salt thereof.

PRIOR ART

Constipation refers to a condition where defecation is difficult or rare, and this is a well-known disease. Known constipation is divided mainly into e.g. functional constipation (acute constipation and various kinds of chronic constipation (for example, atonic constipation, spastic constipation, dyschezia, rectal constipation, chemically inducible constipation etc.)), organic constipation, enteroparalytic ileus, IBS, constipation accompanying IBS, constipation accompanying congenital digestive tract dysfunction, constipation accompanying ileus etc. In defecation in the normal state, stimulation of rectal mucous with intestinal contents transferred to the rectum is transmitted to the central nerve, thus inducing an inclination for the stool while causing the bowels and muscles to be reflectively relaxed and contracted (defecating reflex), while constipation occurs due to defecating functions ruined by autonomic nervous dysfunction occurred in digestive tracts, hyper-absorption of water into intestinal tracts, a reduction in secretion of intestinal mucus, motility hindrance, digestive psychosomatic disease in the digestive organs (for example, irritable bowel syndrome (IBS), a reduction in defecating reflective functions, etc. Many of these obstacles are caused by eating habits, life-style, physical activity, psychogenic background (mental stress, emotional instability, etc.). Recently, such constipation is a serious problem in the fields of nursing and clinical and medical cure. As one of factors, there is a rapid increasing number of old people in the society in recent years and an increase in old peoples requiring nursing. Patients with constipation (for example, atonic constipation) attributable to autonomous nervous dysfunction are rapidly increasing. Another factor is an increase in diseases readily causing a reduction in the motility function of digestive tracts. In particular, diabetes is one of serious diseases, and is problematic as complications to cause a rapid increase in patients with constipation. This is called symptomatic constipation, and also observed in hypothyroidism, sclerodermia, cerebrovascular disturbances, depression, spinal disturbances, electrolyte abnormalities, uremia, interstitial lung disease, pulmonary emphysema and various nerve diseases. In addition to these, there are really many reports on patients with spastic constipation accompanying IBS observed often in youths, on patients with chemically inducible constipation induced by use of morphine in cancer patients, etc.

Prescriptions such as a laxative and an enema are conventionally used in principal therapeutic methods. However, these chemicals easily cause diarrhea upon administration thereof, give physical and mental suffering to the patients and nurses, and usually require a long time until their action appears, and their action is long-lasting. There is also a problem that overuse of an enema also causes disappearance of an inclination for the stool. Further, when the patient has high blood pressure or may have cerebral apoplexy, cerebral infarction, cardiac infarction etc., there is also the situation where an enema should be used inevitably to prevent such diseases. Accordingly, if there is a medicine gently promoting defecation without generating diarrhea, the medicine can be expected to be very useful and advantageous to many patients and nurses, and there is demand for providing the medicament. However, a medicine satisfactory in these aspects is still not found.

As to a defecation-promoting agent not causing diarrhea, on one hand, WO94/16702 and Jpn. J. Pharmacol. (68, 119–123 (1995)) have reported "An agent for treating abnormal dejection comprising as an active ingredient a xanthine derivative which selectively and antagonistically inhibits adenosine $A_1$ receptor or a pharmacologically acceptable salt thereof."

Adenosine is an important regulatory factor involved in many intracellular metabolisms such as regulation of energy levels and CAMP levels in the living body, opening and closing calcium channels, and inflow of calcium ions into cells, and its interaction with adenosine receptors on the surface of a cell is essential for exhibiting these physiological activities. Four kinds of receptor subtypes ($A_1$, $A_{2a}$, $A_{2b}$, $A_3$) have been identified until now. These subtypes are different from one another in their distribution in tissues; that is, the $A_1$ receptor occurs relatively abundantly in the heart, aorta, bladder etc., but hardly occurs in the jejunum and in the proximal colon, the $A_{2a}$ receptor is distributed relatively abundantly in the eyeballs, skeletal muscles etc., the $A_{2b}$ receptor in the proximal colon, eyeballs, lung etc., and the $A_3$ receptor in the spleen, uterus, prostate etc. (Br. J. Pharmacol., 118, 1461–1468 (1996)). Adenosine is involved in various physiological functions such as platelet agglutination, heart beat, contraction of smooth muscles, inflammations, release of neurotransmitters, neurotransmission, release of hormones, cellular differentiation, growth of cells, death of cells, biosynthesis of DNA, etc., thus suggesting the relationship thereof with central nerve diseases, cardiovascular diseases, inflammatory diseases, respiratory diseases, immune diseases etc., so usefulness of adenosine receptor agonists/antagonists against these diseases is expected. In addition to WO94/16702 supra, the relationship between the adenosine receptors and the intestinal tracts has been reported in e.g. the followings 1) to 5):

1) An agent for treating abnormal acceleration of intestinal motility, which comprises an adenosine derivative or a pharmacologically acceptable salt thereof as an active ingredient (JP-A 6-211669);

2) An adenosine $A_1$ receptor-selective antagonist brings about a defecation-promoting action by improving the motility of the intestinal tract via release of acetylcholine in neuroterminal distributed in the intestinal tract (Eur. J. Pharmacol., 264, 91 (1994), Gastroenterology, 104, 1420 (1993), Neuroscience, 67, 159 (1995));

3) An adenosine $A_2$ receptor-selective antagonist had no defecation-promoting action (Jpn. J. Pharmacol., 68, 119–123 (1995), Eur. J. Pharmacol., 64, 91 (1994));

4) Adenosine agonists NECA and CPA were added at 0.1 to 30 µM to rat distal colon longitudinal muscles contracted by stimulation with Carbachol, whereby relaxation was observed, and this action was exhibited more strongly by NECA than CPA and antagonized by 1 µM DPCPX as an adenosine antagonist. The pA2 value (NECA, 6.15 to 6.66; CPA, 6.45 to 6.55) of the antagonistic action of DPCPX suggested that this relaxing action is mediated by $A_2$ receptor, and this action was not antagonized by 10 µM CGS21680 (Naunyn-Schmiedeberg's Arch. Pharmacol., 359, 140–146 (1999)); and 5) By adding an adenosine $A_1/A_2$ agonist NECA or an $A_1$ agonist CPA to guinea pig distal colon longitudinal muscles contracted by electrical stimulation, relaxation was observed, while the action of an $A_{2a}$ agonist CGS21680 was very weak. Further, the relaxing action of NECA was antagonized by DPCPX as $A_1$ antagonist and 8-PT as $A_1/A_2$ antagonist, and the pA2 value of the antagonistic action of the two and their ratio (DPCPX, 8.8; 8-PT, 6.5) suggested that this relaxing action is mediated via $A_1$ receptor. Further, NECA or CPA at a concentration (100 nM) enough to relax the contraction of guinea pig colon longitudinal muscles by electrical stimulation did not exhibit a relaxing action on the contracting action of the muscles stimulated by acetylcholine. From the foregoing, it was suggested that the $A_1$ receptor via which the relaxing action of adenosine on the contraction of guinea pig distal colon longitudinal muscles stimulated by electrical stimulation is mediated, occurs in presynapses at nerve endings and participates in suppression of release of acetylcholine. NECA exhibited a relaxing action ($EC_{50}$; 10.4 µM) on the contracting action of guinea pig distal colon longitudinal muscles stimulated with KCl in the presence of tetrodotoxin, while 1 µM CGS21680 did not act thereon, and CPA acted thereon at a high concentration ($EC_{50}$; 12.6 µM). Further, DPCPX at a concentration (1 nM) enough to selectively inhibit the $A_1$ receptor did not show an antagonistic action, thus indicating that this relaxing action is not mediated via $A_1$ receptor. Further, DPCPX at a concentration (10 nM) enough to inhibit the $A_{2b}$ receptor inhibited the relaxing action of NECA and CPA, and comparison between the pA2 value (NECA; 6.6, CPA; 7.0) in each case and the case (6.6) of DPCPX having the pA2 value (5.7) upon inhibition of the action of NECA by 10 µM 8-PT indicated that this inhibitory action is mediated via $A_{2b}$ receptor. These results indicated that the relaxing action of adenosine on the contraction of guinea pig distal colon longitudinal muscles stimulated with KCl in the presence of tetrodotoxin is mediated via the $A_{2b}$ receptor present in the longitudinal muscles. From these experimental results, it was suggested that adenosine exhibits a relaxing action via the two different receptors, that is, $A_1$ receptor in presynapse and $A_{2b}$ receptor in postsynapse in guinea pig distant colon longitudinal muscles (Br. J. Pharmacol., 129, 871–876 (2000)).

The xanthine derivative not causing diarrhea described in WO94/16702 supra is reported to exhibit a defecation-promoting action based on an adenosine $A_1$ receptor antagonism via cholinergic nerves (Eur. J. Pharmacol., 264, 91 (1994)). Accordingly, it is considered as clinical significance if a strong defecation-promoting action can be exhibited via direct action on the digestive tracts. However, the xanthine derivative exhibits a diuretic action based on an adenosine $A_1$ receptor antagonism (JP-A 3-173889), so its use as a defecation-promoting agent should be significantly limited. This is because assuming its use in patients with complications with renal diseases or old peoples requiring nursing, it is desired that the balance between the diuretic action and defecation-promoting action is shifted toward the defecation-promoting action. From the foregoing, in the treatment of constipation, pharmaceutical preparations promoting defecation gently but strongly without causing diarrhea can be expected to be very useful in patients and nurses. That is, the object of the present invention is to search for and find such medicaments.

DISCLOSURE OF THE INVENTION

The present inventors made extensive study in view of the circumstances described above, and on the basis of literatures on the distribution of adenosine receptors in the intestinal tracts in humans and rats, in which $A_{2b}$ receptor belonging to a subtype of $A_2$ receptor is reported to occur particularly abundantly in the colon (Mol. Endocrinol., 6, 384 (1992), Mol. Pharmacol., 47, 1126 (1995), Br. J. Pharmacol., 118, 1461 (1996)), they established the following new concepts (I) and (II).

(I) The difference in the distribution of adenosine receptors in the colon is related to the functions of the colon. That is, the $A_2$ receptor, particularly $A_{2b}$ receptor, is involved closely in regulation of the functions of the colon.

(II) As for colon motility involved in the defecation, a compound having an adenosine $A_2$ receptor antagonism, particularly a compound having an $A_{2b}$ receptor antagonism, brings about the action of regulating colon motility via a mechanism different from that of the above-mentioned xanthine derivative ($A_1$ antagonist) Then, the present inventors made further extensive study, and a result, they found a compound having an $A_2$ receptor antagonism, particularly a compound having an $A_{2b}$ receptor antagonism, exhibits a gentle but strong defecation-promoting action without causing diarrhea, and the present invention was thereby completed.

That is, the present invention relates to (1) a defecation-promoting agent comprising a compound having an adenosine $A_2$ receptor antagonism or a salt thereof, (2) a defecation-promoting agent comprising a compound having an adenosine $A_{2b}$ receptor antagonism or a salt thereof, (3) the defecation-promoting agent according to the above-mentioned (1) or (2), which is used for treating, preventing or improving a symptom where defecation is difficult and/or rare, (4) the defecation-promoting agent according to the above-mentioned (1) or (2), which is an agent for treating, preventing or improving constipation, (5) the defecation-promoting agent according to the above-mentioned (1) or (2), which is an agent for treating, preventing or improving functional constipation, (6) the defecation-promoting agent according to the above-mentioned (5), wherein the the functional constipation is spastic constipation or atonic constipation, (7) the defecation-promoting agent according to the above-mentioned (1) or (2), which is an agent for treating, preventing or improving irritable bowel syndrome or constipation accompanying irritable bowel syndrome, (8) The defecation-promoting agent according to the above-mentioned (1) or (2), which is an agent for treating, preventing or improving organic constipation, constipation accompanying enteroparalytic ileus, constipation accompanying congenital digestive tract dysfunction or constipation accompanying ileus, (9) the defecation-promoting agent according to the above-mentioned (1) or (2), which is for evacuating intestinal tracts at the time of examination of digestive tracts or before and after an operation, (10) the defecation-promoting agent according to the above-mentioned (1) or (2), wherein the compound is at least one compound selected from 2-amino-4-(2-furyl)-5-(4-pyridyl) pyrimidine, 3-n-propylxanthine, theophylline, caffeine, 1,3-dipropylxanthine, enprophylline, 1-methyl-3-isobutylxanthine, paraxanthine, 8-phenyltheophylline, 1,3-diethyl-8-phenylxanthine, 8-[4-[[[[(2-aminoethyl)amino]carbonyl] methyl]oxy]phenyl]-1,3-dipropylxanthine, 8-[4-[[[methyl-(2-dimethylaminoethyl)-amino]sulfonyl]phenyl]-1,3-dipropylxanthine, 1,3-dimethyl-8-(p-sulfophenyl)xanthine and 1,3-dipropyl-8-(p-sulfophenyl)xanthine, (11) use of a compound having an adenosine $A_2$ receptor antagonism or a salt thereof for producing a defecation-promoting agent, (12) use of a compound having an adenosine $A_{2b}$ receptor antagonism or a salt thereof for producing a defecation-promoting agent, (13) use of an adenosine $A_{2b}$ receptor antagonist for producing an agent for treating, preventing or improving constipation, (14) a compound represented by the formula:

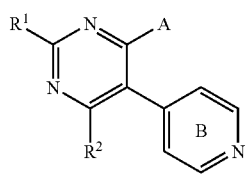

(wherein A represents a phenyl group, pyridyl group, thienyl group or furyl group which may be substituted with one or two groups selected from a halogen atom, a hydroxyl group, a $C_{1-6}$ alkyl group, a $C_{1-6}$ alkoxy group and a $C_{1-6}$ alkoxycarbonyl group;

B represents a pyridyl group which may be substituted with one or more groups selected from a halogen atom, a hydroxyl group, a $C_{1-6}$ alkyl group and an amino group;

$R^1$ represents a hydrogen atom, a morpholinyl group or a group represented by the formula —$NR^{1a}R^{1b}$ (wherein $R^{1a}$ and $R^{1b}$ are the same as or different from each other and each represents a hydrogen atom, a $C_{1-6}$ alkyl group, a $C_{1-6}$ acyl group, a phenyl group or a $C_{1-6}$ alkylsulfonyl group); and $R^2$ represents a hydrogen atom or a group represented by the formula —$NR^{2a}R^{2b}$ (wherein $R^{2a}$ and $R^{2b}$ are the same as or different from each other and each represents a hydrogen atom or a $C_{1-6}$ alkyl group), provided that, in the above definition, the cases where (i) A is a 4-fluorophenyl group; B is a 4-pyridyl group; -$R^1$ is an amino group; and $R^2$ is a hydrogen atom, and (ii) A is a 4-fluorophenyl group; B is a 4-pyridyl group; $R^1$ is an acetamide group; and $R^2$ is a hydrogen atom are excluded) or a salt thereof, (15) a compound represented by the formula:

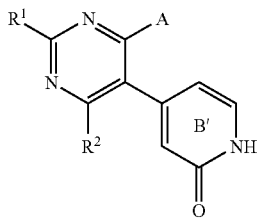

(wherein A, $R^1$ and $R^2$ have the same meanings as defined in the above-mentioned (16); and B' is a 1,2-dihydro-2-pyridinone-4-yl group which may be substituted with one or more groups selected from a halogen atom, a hydroxyl group, a $C_{1-6}$ alkyl group and an amino group) or a salt thereof, (16) a pharmaceutical composition comprising the compound described in the above-mentioned (14) or (15), or a salt of them, (17) the composition according to the above-mentioned (16), which is an adenosine $A_{2b}$ receptor antagonist, (18) the composition according to the above-mentioned (16), which is a defecation-promoting agent, (19) the composition according to the above-mentioned (16), which is an agent for treating, preventing or improving constipation, (20) the composition according to the above-mentioned (16), which is an agent for treating, preventing or improving functional constipation, (21) the composition according to the above-mentioned (20), wherein the functional constipation is spastic constipation or atonic constipation, (22) The composition according to the above-mentioned (16), which is an agent for treating, preventing or improving irritable bowel syndrome or constipation accompanying irritable bowel syndrome, (23) the composition according to the above-mentioned (16), which is an agent for treating, preventing or improving organic constipation, constipation accompanying enteroparalytic ileus, constipation accompanying congenital digestive tract dysfunction or constipation accompanying ileus, and (24) the composition according to the above-mentioned (16), which is for evacuating intestinal tracts at the time of examination of digestive tracts or before and after an operation.

The present invention provides a method for promoting defecation, by administering a pharmacologically effective amount of a compound having an adenosine $A_2$ receptor antagonism or a salt thereof to a patient, a method for promoting defecation, by administering a pharmacologically effective amount of a compound having an adenosine $A_{2b}$ receptor antagonism or a salt thereof to a patient, and a method for treating, preventing or improving constipation, by administering a pharmacologically effective amount of a compound having an adenosine $A_{2b}$ receptor antagonism or a salt thereof to a patient.

The present invention relates to use of a compound represented by the formula (I) or (II) or a salt of them for producing a defecation-promoting agent, and to use of a compound represented by the formula (I) or (II) or a salt of them for producing an agent for treating, preventing or improving constipation.

The present invention relates to a method for promoting defecation, by administering a pharmacologically effective amount of a compound represented by the formula (I) or (II) or a salt of them to a patient, and to a method for treating, preventing or improving constipation, by administering a pharmacologically effective amount of a compound represented by the formula (I) or (II) or a salt of them to a patient.

Hereinafter, the meanings of symbols, terms, etc. used in the present specification are described, and the present invention is described in detail.

In this specification, the "defecation-promoting agent" refers to a pharmaceutical composition promoting physiological defecation.

In this specification, the "constipation" refers to conditions where defecation is felt to be difficult or is rare, and includes various kinds of constipation such as functional constipation, organic constipation, enteroparalytic ileus, IBS, constipation accompanying IBS, constipation accompanying congenital digestive tract dysfunction and constipation accompanying ileus. Further the "constipation" also includes conditions with some sufferings and difficulties even in a small amount of defecation. Herein, the functional constipation refers to acute constipation and various kinds of chronic constipation (for example, atonic constipation, spastic constipation, dyschezia, rectal constipation, chemically inducible constipation etc.).

In this specification, the "compound" refers to both non-peptide compound and peptide compound. The "compound" may form a salt, or may form either an anhydride or a hydrate.

In this specification, the "salt" is not particularly limited insofar as it is a pharmacologically acceptable salt of the compound having an $A_2$ receptor antagonism or the compound having an $A_{2b}$ receptor antagonism, and preferable examples thereof include 1) hydrohalogenic acid salts (for example, hydrofluoride, hydrochloride, hydrobromide and hydroiodide); 2) inorganic acid salts (for example, sulfate, nitrate, perchlorate, phosphate, carbonate and bicarbonate); 3) organic carboxylic acid salts (for example, acetate, oxalate, maleate, tartrate and fumarate); 4) organic sulfonic acid salts (for example, methanesulfonate, trifluoromethanesulfonate, ethanesulfonate, benzenesulfonate, toluenesulfonate and camphor sulfonate); 5) amino acid salts (for example, aspartate and glutamate); 6) quaternary amine salts; 7) alkali metal salts (for example, sodium salt and potassium salt); and 8) alkaline earth metal salts (for example, magnesium salt and calcium salt).

In this specification, the "antagonism" refers to the action of inactivating by blocking the interaction of the adenosine receptor with its ligand (adenosine), that is, by blocking the binding of the ligand to the receptor. The "compound having an antagonism" refers to a compound having the action of inactivating by blocking the binding of the ligand (adnosine) to the adenosine receptor.

Hereinafter, Test Examples are described to demonstrate that the pharmaceutical composition according to the present invention is useful as a pharmaceutical composition (referred to hereinafter as "defecation-promoting agent") promoting defecation (Test Examples 1 to 3). The compounds used in the test are compounds represented by the formulae:

Compound I: 2-Amino-4-(2-furyl)-5-(4-pyridyl)pyrimidine

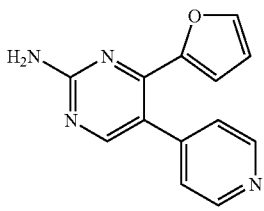

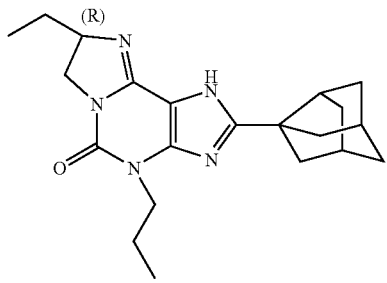
KF20274

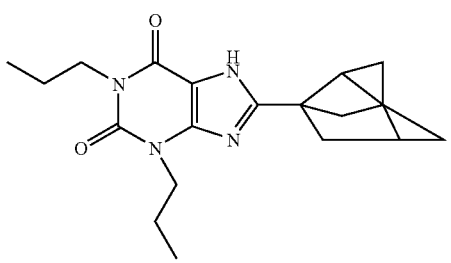
KW3902

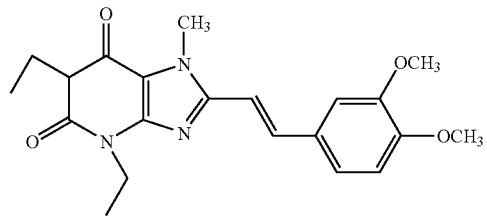
KW6002

Compound I is a novel $A_{2b}$ receptor antagonist (Example No. 3) found by the present inventors. On one hand, KF20274 and KW3902 are known as selective $A_1$ receptor antagonists, while KW6002 is known as a selective $A_{2a}$ receptor antagonist. The ability of these compounds to bind to adenosine receptor subtype and the inhibitory ability thereof are shown below (Table 6). KF20274 was produced by a process described in J. Med. Chem., Vol. 35, No. 19, 3578–3581 (1992), KW3902 by a process in J. Med. Chem., Vol. 35, No. 5, 924–930 (1992), and KW6002 by a process in Bioorg. & Med. Chem. Lett., Vol. 7, No. 18, 2349–2352 (1997).

Test Example 1

Inhibitory Effect of Adenosine $A_{2b}$ Receptor Antagonist on Suppressing Action of NECA on Carbachol-Stimulated Contraction of Colon (1) Excision of the Colon The abdomen of a rat under anesthesia with ether was opened, and from the rectum to the cecum was excised therefrom and soaked in ice-cooled Tyrode solution (containing 136 mM NaCl, 2.7 mM KCl, 0.4 mM $NaH_2PO_4.2H_2O$, 5.6 mM glucose, 11.9 mM $NaHCO_3$, 1 mM $MgCl_2.6H_2O$, 1.8 mM $CaCl_2$). Surrounding connective tissues were removed, and the intestinal tract was cut at positions apart by 1.5 cm from the rectum and by 3 cm from the cecum, to give a colon tract of about 3 cm in full length. Both the terminals of the colon tract were pinched respectively with Serrefines (trade name) to which a string had been connected, and the colon tract with the side of the cecum facing upward was immediately suspended in a Magnus tube filled with Tyrode solution previously warmed at 37° C., and then equilibrated by bubbling with a gas ($O_2/CO_2$=95/5). The string connected to the Serrefines (trade name) at the side of the cecum was suspended, and the change in the length of the colon tract was detected with an amplifier for strain pressure (Nihon Kohden Corporation).

(2) Contraction of the Colon Tract with Carbachol

Carbachol (Sigma) at each concentration diluted 100-fold was added accumulatively in a volume of 1/100 to the Magnus tube, and the change in the length of the colon tract was measured, and the length thereof in the absence of Carbachol was regarded as 0% contraction, and the length thereof in the presence of 1.44 μM Carbachol was regarded as 100% contraction. In the experiment, 3 samples were used.

(3) Inhibitory Effect of NECA on Carbachol-Stimulated Contraction of the Colon Tract To the colon tract in the presence of 1.44 μM Carbachol in the Magnus tube was added accumulatively a volume of 1/100 of NECA (Sigma) diluted 100-fold, and the change in the length of the colon tract was measured. Assuming that the length thereof in the absence of Carbachol was regarded as 0% contraction while the length thereof in the presence of 1.44 μM Carbachol was regarded as 100% contraction, the contraction thereof in the presence of NECA was determined. In the experiment, 3 samples were used.

(4) Inhibitory Effect of Adenosine Receptor Antagonist on Suppressing Action of NECA on Carbachol-Stimulated Contraction of the Colon Tract 0.3 μM Carbachol and 1 μM NECA were successively added to the colon tract, and Compound I, KF20274 or KW6002 diluted 100-fold was accumulatively added in a volume of 1/100 to the Magnus tube, and the change in the length of the colon tract was measured. Assuming that the length thereof in the presence of 0.3 μM Carbachol and 1 μM NECA was regarded as 0% contraction while the length thereof in the presence of 0.3 μM Carbachol only was regarded as 100% contraction, the contraction in the presence of each of the adenosine receptor antagonists was determined. In the experiment, 3 samples were used.

By stimulation with Carbachol (the above operation 2), the colon tract showed contraction in a manner dependent on the concentration of Carbachol (Table 1). When the adenosine receptor agonist NECA was added thereto (the above operation 3), its inhibitory effect on the contraction was observed in a manner depending on the concentration of NECA (Table 2). Carbachol has nicotinic and muscarinic acetylcholine receptor-stimulating actions in autonomic ganglions and smooth muscles respectively, so the inhibitory effect of NECA on the contraction could not be elucidated only by its action working via nerves distributed in smooth muscles, thus suggesting the possibility of its direct action on smooth muscles. Further, when each antagonist for adenosine receptor was added to this system (the above operation 4), Compound I inhibited the suppressing effect of NECA on the contraction, in a manner depending on the concentration of Compound I (Table 3). On one hand, the $A_1$-selective antagonist KF20724 and $A_{2a}$-selective antagonist KW6002 did not show any inhibitory effect. This indicates that the contraction-suppressing effect of NECA is not an action mediated via $A_1$ and $A_{2a}$ receptors, thus suggesting the involvement of $A_{2b}$ receptor. It was thus suggested that adenosine could suppress contraction of the colon directly via the $A_{2b}$ receptor in colon smooth muscles, and the present inventors succeeded in directly demonstrating that the $A_{2b}$ receptor antagonist could antagonize to promote contraction of the colon.

TABLE 1

| Carbachol (μM) | Contraction (%) | |
| --- | --- | --- |
| | Mean | Standard Error |
| 0.01 | 1.4 | 1.4 |
| 0.04 | 24.5 | 10.4 |
| 0.14 | 69.1 | 5.5 |
| 0.44 | 87.0 | 2.4 |
| 1.44 | 100.0 | 0.0 |

TABLE 2

| NECA (μM) | Contraction (%) | |
| --- | --- | --- |
| | Mean | Standard Error |
| 0.1 | 89.0 | 3.2 |
| 0.4 | 75.3 | 4.9 |
| 1.4 | 63.1 | 6.8 |
| 4.4 | 59.2 | 4.6 |
| 14.4 | 54.9 | 8.9 |

Carbachol 1.44 μM (singly added) = 100%

TABLE 3

| | Contraction (%) | |
| --- | --- | --- |
| | Mean | Standard Error |
| Compound I (μM) | | |
| 0.1 | 71.5 | 36.2 |
| 0.4 | 111.0 | 51.9 |
| 1.4 | 122.0 | 53.1 |
| 4.4 | 85.9 | 35.6 |
| KW20274 (μM) | | |
| 0.1 | −8.2 | 4.8 |
| 0.4 | −26.0 | 20.7 |
| 1.4 | −40.0 | 24.2 |
| 4.4 | −71.0 | 35.7 |
| KW6002 (μM) | | |
| 0.1 | 5.2 | 3.4 |
| 0.4 | 1.1 | 4.2 |
| 1.4 | −2.9 | 3.3 |
| 4.4 | −3.9 | 7.8 |

Carbachol 0.3 μM + NECA 1 μM = 0%
Carbachol 0.3 μM (singly added) = 100%

Test Example 2

Defecation-Promoting Action of the Adenosine $A_{2b}$ Receptor Antagonist in Rat The present inventors examined and compared the action of the $A_{2b}$ receptor antagonist (Compound I), the $A_1$-selective antagonist or the $A_{2a}$-selective antagonist on defecation in rats.

SD IGS rats (6-weeks-old, from Charles River) were placed in cages (3 animals/cage) and preliminarily allowed food and water ad libitum and raised for 1 week. On the day of the experiment, their weight was measured, a water-absorbing sheet was placed below each cage, and the animals were fasted but allowed water ad libitum throughout the experiment. Three hours after fasting was initiated, the fecal pellets were recovered from each cage and observed for abnormality before the experiment, and then the compound suspended or dissolved in 0.5% (W/V) methyl cellulose (MC) was orally administered into each rat in a dose of 5 ml/kg. On one hand, 0.5% (W/V) MC only was orally given to the control group. After administering the compound, the rats were returned to the cage provided with a new water-absorbing sheet of known weight, and 180 minutes after the administration, the fecal pellets on the water-absorbing sheet were recovered from each cage, and the external appearance was observed, and the number of fecal pellets was counted. The number of fecal pellets is expressed per each cage (Table 4). After the fecal pellets were recovered, the water-absorbing sheet was weighed, and the weight determined by subtracting the initial weight of the water-adsorbing sheet from the weight after the experiment was regarded as the volume of urine and expressed as the volume of urine per 100 g of the body weight (Table 4).

TABLE 4

| Compound | Dose | The number of fecal pellets/3 rats | Urine Volume (g/100 g body weight) |
|---|---|---|---|
| Control | — | 1.00 ± 0.68 | 0.89 ± 0.10 |
| Compound I | 3 mg/kg | 16.33 ± 1.82 | 0.79 ± 0.09 |
|  | 10 mg/kg | 30.00 ± 2.79 | 1.23 ± 0.13 |
| KW3902 | 0.3 mg/kg | 10.67 ± 2.08 | 2.08 ± 0.04 |
|  | 1 mg/kg | 14.50 ± 1.18 | 2.15 ± 0.09 |
|  | 3 mg/kg | 12.83 ± 1.66 | 2.01 ± 0.06 |
| KW6002 | 1 mg/kg | 6.67 ± 1.63 | 0.72 ± 0.07 |
|  | 3 mg/kg | 7.00 ± 0.86 | 0.76 ± 0.05 |

As shown in Table 4, the $A_1$-selective receptor antagonist KW3902 exhibits a defecation-promoting action, but this action can be seen to reach the maximum in a dose of 1 mg/kg. Further, the $A_{2a}$-selective receptor antagonist KW6002 had a low defecation-promoting action. On one hand, the $A_{2b}$ receptor antagonist Compound I did not cause diarrhea and showed an evidently higher defecation-promoting action than the $A_1$-selective antagonist KW3902 or the $A_{2a}$-selective antagonist KW6002. Compound I is a compound also having an antagonistic, inhibitory action on $A_1$ receptor, but this strong defecation-promoting action cannot be elucidated in terms of the absorption or different dose of the compound having an antagonistic, inhibitory action on $A_1$ receptor. This is because compounds having an antagonistic, inhibitory action on $A_1$ receptor are well known to have a diuretic action (J. Pharmacol. Exp. Ther., 266, 200 (1993)), but the $A_1$-selective antagonist KW3902 has a stronger diuretic action than Compound I, while its defecation-promoting action is weaker than Compound I. On the other hand, Compound I has a weaker diuretic action than the $A_1$-selective antagonist KW3902, whereas its defecation-promoting action is stronger.

That is, Table 4 shows that the action of Compound I cannot be elucidated only by the antagonistic action on $A_1$ receptor, and that the stronger defecating action was brought about by adding the antagonistic, inhibitory action on $A_{2b}$ receptor. Test Example 3 Contribution of inhibition of adenosine $A_{2b}$ receptor to defecation-promoting action For the purpose of further examination of contribution of the antagonistic inhibitory action of Compound I on $A_{2b}$ receptor to the strong defecation-promoting action thereof, a combination of the $A_1$-selective antagonist KW3902 and the $A_{2a}$-selective antagonist KW6002 was administered and compared with Compound I. Test rats and the compounds were raised and prepared in the same manner as in Test 1. After administering the compounds, the rats were returned to the cage under which a new water-absorbing sheet had been installed, and after 180 minutes, the fecal pellets on the water-absorbing sheet were recovered from each cage, and the outward appearance was observed and the number of fecal pellets was counted. The number of fecal pellets is expressed per cage (Table 5).

TABLE 5

| Compound | Dose | KW6002 (1 mg/kg) | The number of fecal pellets/3 rats |
|---|---|---|---|
| Control | — | − | 2.50 ± 0.65 |
| Compound I | 3 mg/kg | − | 34.00 ± 1.00 |

TABLE 5-continued

| Compound | Dose | KW6002 (1 mg/kg) | The number of fecal pellets/3 rats |
|---|---|---|---|
| KW3902 | 0 mg/kg | + | 7.00 ± 1.58 |
|  | 1 mg/kg | − | 9.00 ± 1.08 |
|  | 1 mg/kg | + | 18.25 ± 1.49 |

In Test Example 3, the $A_1$-selective antagonist KW3902 was administered in a dose enough to exhibit a diuretic action. As shown in Table 5, when the $A_1$-selective antagonist KW3902 and the $A_{2a}$-selective antagonist KW6002 were simultaneously administered, both their respective defecation-promoting actions were brought about. Accordingly, a compound having both an antagonistic action on $A_1$ receptor and an antagonistic action on $A_{2a}$ receptor is considered to exhibit a stronger defecation-promoting action than by a single $A_1$-selective antagonist. However, their action did not reach the defecation-promoting action of Compound I as the $A_{2b}$ receptor antagonist. That is, the result in Table 5 shows that the contribution of $A_{2b}$ receptor antagonism is very important for promotion of defecation.

Comprehensive Discussion

The test revealed that the compound antagonistically inhibiting $A_{2b}$ receptor exhibits a strong defecation-promoting action without causing diarrhea, and its action is further stronger than that of the $A_1$-selective antagonist. Accordingly, a pharmaceutical preparation comprising the compound having an $A_{2b}$ receptor antagonism or a salt thereof is useful as a defecation-promoting agent, and in particular a pharmaceutical preparation comprising the $A_{2b}$ receptor antagonist is very useful. It is therefore evident that the defecation-promoting agent of the invention is useful as an agent for treating, preventing or improving various kinds of constipation, and can exhibit an excellent effect as an agent for treating, preventing or improving for example functional constipation (acute constipation and various kinds of chronic constipation (for example, atonic constipation, spastic constipation, dyschezia, rectal constipation, chemically inducible constipation etc.)), organic constipation, enteroparalytic ileus, IBS, constipation accompanying IBS, constipation accompanying congenital digestive tract dysfunction, constipation accompanying ileus etc. Further, use of the defecation-promoting agent of the invention as a pharmaceutical preparation is very useful not only for treating, preventing or improving various kinds of constipation, but also as a chemical for evacuating intestinal tracts at the time of examination of digestive tracts or before and after an operation, as an aid for defecation after an operation, and as a chemical for promoting defecation after administering a contrast medium. Measurement of the ability of the compound to bind to and inhibit the receptors The ability of the compound to bind to and the ability thereof to inhibit each subtype of adenosine receptor was measured in a known method described below.

1) Measurement of the Ability to Bind to Adenosine $A_1$ Receptor

A human adenosine $A_1$ receptor cDNA was expressed in excess in CHOK1 cells, and this membrane sample was added at a protein concentration of 66.7 μg/ml to, and suspended in, 20 mM HEPES buffer, pH 7.4 (10 mM $MgCl_2$, 100 mM NaCl). To 0.45 ml of this membrane sample suspension were added 0.025 ml of 60 nM tritium-labeled chlorocyclopentyl adenosine ($^3$H-CCPA, from NEN Ltd.) and 0.025 ml test compound. This mixture was left at 30° C.

for 120 minutes, filtered rapidly under suction through a glass fiber filter (GF/B, from Whatman), and immediately washed twice with 5 ml of 50 mM water-cooled Tris-HCl buffer. Thereafter, the glass fiber filter was transferred to a vial, a scintillator was added thereto, and the radioactivity on the filter was measured by a liquid scintillation counter. The inhibition of binding of $^3$H-CCPA to $A_1$ receptor by the test compound was determined using the following formula, and from this inhibition, 50% inhibition concentration ($IC_{50}$) was calculated (the following equation).

Inhibition (%)=[1-{binding in the presence of the test compound-non-specific binding)/(total binding-non-specific binding)}]×100

In the above formula, the total binding means $^3$H-CCPA-bound radioactivity in the absence of the test compound; the non-specific binding means $^3$H-CCPA-bound radioactivity in the presence of 100 µM RPIA ([R]-[1-methyl-2-phenylethyl] adenosine); and the binding in the presence of the test compound means $^3$H-CCPA-bound radioactivity in the absence of the test compound at predetermined concentrations. The inhibition constant (Ki value) in the table was determined from the formula of Cheng-Prusoff.

2) Measurement of the Ability to Bind to Adenosine $A_{2a}$ Receptor

An experiment of inhibition of binding to adenosine $A_{2a}$ receptor was conducted using a membrane sample (Receptor Biology Inc.) where an adenosine $A_{2a}$ receptor cDNA was expressed in excess. This membrane sample was added at a protein concentration of 22.2 µg/ml to, and suspended in, 20 mM HEPES buffer, pH 7.4 (10 mM $MgCl_2$ and 100 mM NaCl). To 0.45 ml of this membrane sample suspension were added 0.025 ml of 500 nM tritium-labeled 2-p-[2-carboxyethyl]phenetylamino-5'-N-ethylarboxyamide adenosine ($^3$H-CGS21680, from NEN) and 0.025 ml test compound. This mixture was left at 25° C. for 90 minutes, filtered rapidly under suction through a glass fiber filter (GF/B, from Whatman), and immediately washed twice with 5 ml of 50 mM water-cooled Tris-HCl buffer. Thereafter, the glass fiber filter was transferred to a vial, a scintillator was added thereto, and the radioactivity on the filter was measured by a liquid scintillation counter. The inhibition of binding of $^3$H-CGS21680 to $A_{2a}$ receptor by the test compound was determined using the following formula, and from this inhibition, 50% inhibition concentration ($IC_{50}$) was calculated.

Inhibition (%)=[1-{binding in the presence of the test compound-nonspecific binding)/(total binding-nonspecific binding)}]×100

In the above formula, the total binding means $^3$H-CGS21680-bound radioactivity in the absence of the test compound; the nonspecific binding means $^3$H-CGS21680-bound radioactivity in the presence of 100 µM RPIA; and the binding in the presence of the test compound means $^3$H-CGS21680-bound radioactivity in the absence of the test compound at predetermined concentrations. The inhibition constant (Ki value) in the table was determined from the formula of Cheng-Prusoff.

3) Experiment of Inhibition of NECA-Stimulated Production of cAMP in Adenosine $A_{2b}$ Receptor-Expressing Cells CHOK1 cells where a human adenosine $A_{2b}$ receptor had been expressed in excess were plated onto a 24-well plate at a density of $1.5×10^5$ cells/well, cultured overnight, and used in the experiment. The degree of inhibitory effect of the test compound on the amount of cAMP produced by stimulation with 30 nM 5'-N-ethylcarboxyamide adenosine (NECA from Sigma) was evaluated in terms of affinity for $A_{2b}$ receptor. That is, the adhering cells were washed twice with 2 ml/well Krebs-Ringer buffer solution (containing 0.1% BSA; pH 7.4) and pre-incubated for 30 minutes in a volume of 0.5 ml/well. Then, a mixed solution containing NECA and the test compound was added in a volume of 0.1 ml/well in the presence of a phosphodiesterase inhibitor Ro-20-1724 (a product of RBI). After pre-incubation for 15 minutes, the reaction was terminated with 0.1 N HCl in a volume of 300 µl/well. Measurement of intracellular cAMP was carried out using a cAMP enzyme immunoassay kit produced by Amersham. The inhibition of NECA-stimulated production of cAMP by the test compound was determined using the following equation:

Inhibition (%)=[1-{(amount of cAMP in the coexistence of NECA and the test compound-amount of cAMP in only the Krebs-Ringer buffer solution)/(amount of cAMP upon stimulation with NECA only-amount of cAMP in only the Krebs-Ringer buffer solution)}]×100

From the inhibition thus determined, 50% inhibition concentration ($IC_{50}$) was determined.

The results of the experiment of measuring the ability to bind to, and the ability to inhibit, each receptor are as follows (Table 6).

TABLE 6

| Test Compound | $A_1$ receptor Ki (nM) | $A_{2a}$ receptor Ki (nM) | $A_{2b}$ receptor $IC_{50}$ (nM) |
| --- | --- | --- | --- |
| Compound I | 660 | 112 | 8.4 |
| KW3902 | 10 | 40 | 126 |
| KW6002 | 22600 | 52 | 2850 |

Those skilled in the art to which the present invention belongs can measure the ability of any compounds to bind to, or to inhibit, the adenosine receptor subtype thereby identifying a compound having an $A_2$ receptor antagonism and a compound having an $A_{2b}$ receptor antagonism.

Until now, the compounds shown below or a salt thereof (compounds shown in (1) to (27) below) are known as compounds exhibiting an $A_{2b}$ receptor antagonism. The antagonistic action of these known compounds on $A_{2b}$ receptor can be confirmed in the tests described above. These compounds and/or a salt thereof are useful as the active ingredient in the defecation-promoting pharmaceutical composition according to the present invention.

(1)

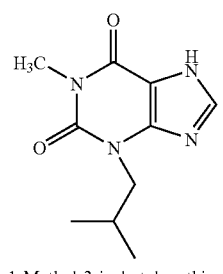

1-Methyl-3-isobutylxanthine

-continued (2)

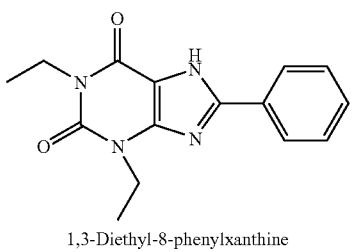

1,3-Diethyl-8-phenylxanthine (3)

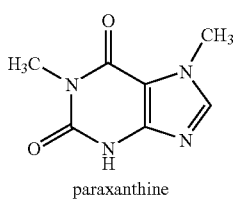

paraxanthine (4)

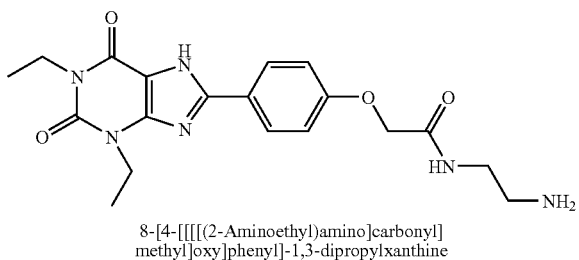

8-[4-[[[[(2-Aminoethyl)amino]carbonyl]
methyl]oxy]phenyl]-1,3-dipropylxanthine (5)

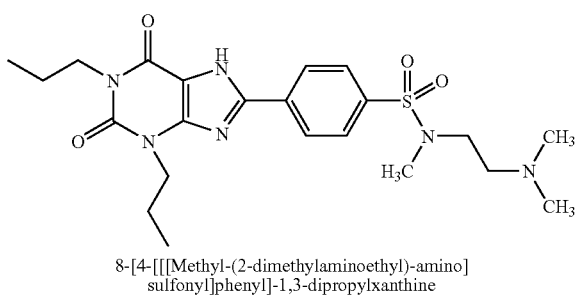

8-[4-[[[Methyl-(2-dimethylaminoethyl)-amino]
sulfonyl]phenyl]-1,3-dipropylxanthine (6)

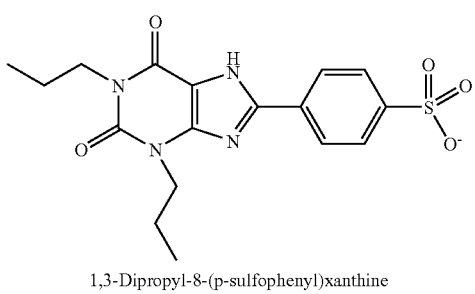

1,3-Dipropyl-8-(p-sulfophenyl)xanthine (7)

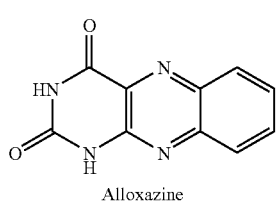

Alloxazine (8) 2,4-Dioxobenzo[g]pteridine (9) Purine derivatives represented by the formula:

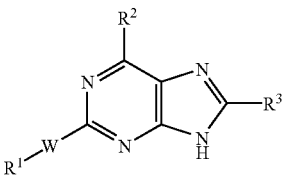

(wherein $R^1$ means the formula:

(wherein X represents a hydrogen atom, a hydroxyl group, a lower alkyl group which may have a substituent group, a lower alkoxy group which may have a substituent group, an aryl group which may have a substituent group, a heteroaryl group which may have a substituent group, an acyl group which may have a substituent group, an acyloxy group which may have a substituent group or an amino group which may have a substituent group; and $R^5$ and $R^6$ are the same as or different from each other and each represents a hydrogen atom, a lower alkyl group which may have a substituent group, a saturated or unsaturated $C_{3-8}$ cycloalkyl group which may have a substituent group, a $C_{3-8}$ cycloalkyl-$C_{2-6}$ alkyl group which may have a substituent group, an aryl group which may have a substituent group, a heteroaryl group which may have a substituent group, a carboxyl group which may have a protective group or a 4- to 6-memberred ring having at least one heteroatom which may have a substituent group, or $R^5$ and $R^6$ together represent an oxygen atom or sulfur atom, or together with the carbon atom to which they bind, represent a ring which may have a heteroatom and a substituent group) or (2) a 5- or 6-memberred aromatic ring which may have a substituent and a heteroatom;

W means a group represented by the formula —$CH_2CH_2$—, —CH=CH— or —C≡C—;

$R^2$ represents a hydrogen atom, a lower alkyl group which may have a substituent group, a hydroxyl group or the formula —$NR^7R^8$ (wherein $R^7$ and $R^8$ are the same as or different from each other and represents a hydrogen atom, a hydroxyl group, a $C_{1-6}$ alkyl group which may have a substituent group, an acyl group which may have a substituent group, a $C_{3-8}$ cycloalkyl group which may have a substituent group, an aryl group which may have a substituent group or a heteroaryl group which may have a substituent group, or $R^7$ and $R^8$ together with the nitrogen atom to which they bind form a saturated ring which may have a heteroatom or a substituent group);

$R^3$ represents a hydrogen atom, a $C_{3-8}$ cycloalkyl group which may have a substituent group, an aryl group which may have a substituent group, a heteroaryl group which may have a substituent group or a $C_{2-6}$ alkenyl group which may have a substituent group; and $R^4$ represents a hydrogen atom, a lower alkyl group which may have a substituent group, a $C_{3-8}$ cycloalkyl group which may have a substituent group, an aryl group which may have a substituent group, a heteroaryl group which may have a substituent group, a $C_{2-6}$ alkenyl group which may have a substituent group, a $C_{2-6}$ alkynyl group which may have a substituent group or a cyclic ether which may have a substituent group, provided that the case where 1) W is —$CH_2CH_2$—; and X is a hydrogen atom or an alkyl group and the case where 2) W is —C=C—; $R^3$ is a hydrogen atom; and $R^4$ is a cyclic ether which may have a substituent group are excluded), a pharmaceutically acceptable salt thereof or a hydrate of them (JP-A 11-263789).

(10) Purine compounds represented by the formula:

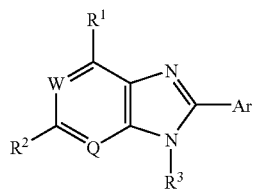

(wherein $R^1$ represents (1) a hydrogen atom, (2) a hydroxyl group, (3) a halogen atom, (4) a $C_{1-8}$ alkyl group which may have a substituent group or (5) the formula —$NR^4R^5$ (wherein $R^4$ and $R^5$ are the same as or different from each other and each represents a hydrogen atom, a $C_{1-8}$ alkyl group or a $C_{3-8}$ cycloalkyl group, or together with the nitrogen atom to which they bind, represents a $C_{2-5}$ saturated cyclic amino group which may, in addition to the nitrogen atom, contain an oxygen atom, a sulfur atom or a nitrogen atom, and may be further substituted with a $C_{1-4}$ alkyl group which may be substituted with a halogen atom;

$R^2$ represents (1) a hydrogen atom, (2) a halogen atom, (3) a group represented by the formula —$NR^6R^7$ (wherein $R^6$ and $R^7$ are the same as or different from each other and each represents a hydrogen atom, a $C_{2-5}$ acyl group, a $C_{1-8}$ alkyl group or a $C_{3-8}$ cycloalkyl group, or $R^6$ and $R^7$ together with the nitrogen atom to which they bind form a $C_{2-5}$ saturated cyclic amino group which may, in addition to the nitrogen atom, contain an oxygen atom, a sulfur atom or a nitrogen atom, and may be further substituted with a $C_{1-4}$ alkyl group which may be substituted with a halogen atom, (4) a $C_{2-8}$ alkynyl group which may be substituted with a halogen atom, a hydroxyl group, a $C_{1-4}$ alkyl group or a $C_{3-6}$ cyloalkyl group, (5) a $C_{3-8}$ alkenyl group which may be substituted with a halogen atom, a hydroxyl group or a $C_{1-4}$ alkyl group, (6) a $C_{1-8}$ alkyl group which may be substituted with a halogen atom, a hydroxyl group or a $C_{1-4}$ alkyl group or (7) a $C_{1-8}$ alkoxy group which may be substituted with a halogen atom, a hydroxyl group or a $C_{1-4}$ alkyl group;

$R^3$ represents (1) a $C_{3-8}$ alkynyl group which may be substituted with a halogen atom, a hydroxyl group or a $C_{1-4}$ alkyl group, (2) a $C_{3-8}$ alkenyl group which may be substituted with a halogen atom, a hydroxyl group or a $C_{1-4}$ alkyl group, (3) a $C_{1-8}$ alkyl group which may be substituted with a halogen atom, a hydroxyl group or a $C_{1-4}$ alkyl group, (4) an aryl group which may have a substituent group, (5) a heteroaryl group which may have a substituent group, (6) an 1,2-dihydro-2-oxopyridyl group which may be substituted with (a) a halogen atom or a $C_{1-6}$ alkyl group, and whose nitrogen atom may be substituted with (b-1) a $C_{1-6}$ alkyl group which may be substituted with a halogen atom, a hydroxyl group or a carboxyl group which may have a protective group, (b-2) a $C_{3-6}$ cycloalkyl-$C_{1-4}$ alkyl group which may have a substituent group or (b-3) a $C_{3-6}$ cycloalkyl group which may have a substituent group, (7) a dihydrooxopyrimidyl group which may be substituted with (a) a halogen atom or a $C_{1-6}$ alkyl group, and whose nitrogen atom is substituted with (b-1) a $C_{1-6}$ alkyl group which may be substituted with a halogen atom, a hydroxyl group or a carboxyl group which may have a protective group, (b-2) a $C_{3-6}$ cycloalkyl-$C_{1-4}$ alkyl group which may have a substituent group or (b-3) a $C_{3-6}$ cycloalkyl group, or (8) a dihydrooxo- or tetrahydrodioxopyrazinyl group which may be substituted with (a) a halogen atom or a $C_{1-6}$ alkyl group, and which may be substituted with a halogen atom, a hydroxyl group or a carboxyl group which may have a protective group, (b-2) a $C_{3-6}$ cycloalkyl-$C_{1-4}$ alkyl group which may have a substituent group or (b-3) a $C_{3-6}$ cycloalkyl group;

Ar represents (1) an aryl group which may have a substituent group, (2) a heteroaryl group which may have a substituent group, (3) an oxopyridyl group which may be substituted with a halogen atom or a $C_{1-6}$ alkyl group and whose nitrogen atom is substituted with a $C_{1-6}$ alkyl group or a $C_{3-6}$ cycloalkyl group, or (4) an oxopyrimidyl group which may be substituted with a halogen atom or a $C_{1-6}$ alkyl group and whose nitrogen atom is substituted with a $C_{1-6}$ alkyl group or a $C_{3-6}$ cycloalkyl group; and Q and W are the same as or different from each other and each represents N or CH, provided that, in the above, when $R^2$ is 1) a $C_{2-8}$ alkynyl group which may be substituted with a halogen atom, a hydroxyl group, a $C_{1-4}$ alkyl group or a $C_{3-6}$ cycloalkyl group; 2) a $C_{3-8}$ alkenyl group which may be substituted with a halogen atom, a hydroxyl group or a $C_{1-4}$ alkyl group or 3) a $C_{1-8}$ alkyl group which may be substituted with a halogen atom, a hydroxyl group or a $C_{1-4}$ alkyl group, $R^3$ is not 1) a $C_{1-8}$ alkyl group which may be substituted with a halogen atom, a hydroxyl group or a $C_{1-4}$ alkyl group, or is not 2) an aryl group which may have a substituent group), a pharmaceutically acceptable salt thereof or a hydrate of them (WO 2001/2400).

(11) Pyrrolo[2,3d]pyrimidine derivatives represented by the formula:

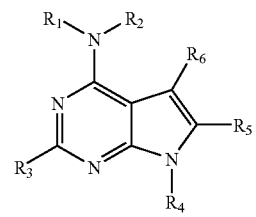

wherein $R_1$ and $R_2$ independently represent a hydrogen atom, an alkyl group which may have a substituent group, an aryl group which may have a substituent group, an alkyl aryl group which may have a substituent group or a hetero ring which may have a substituent formed by each other;

$R_3$ represents a hydrogen atom, an alkyl group which may have a substituent group, an aryl group which may have a substituent group or an alkyl aryl group which may have a substituent group;

$R_4$ represents a hydrogen atom, an alkyl group which may have a substituent group, an aryl group which may have a substituent group or an alkyl aryl group which may have a substituent group; and $R_5$ and $R_6$ independently represent a hydrogen atom, an alkyl group which may have a substituent group, an aryl group which may have a substituent group or an alkyl aryl group which may have a substituent group, or $R_4$ and $R_5$, or $R_5$ and $R_6$ may be combined with each other to form a heterring or hydrocarbon ring which may have a substituent group (WO9962518).

(12) 8-Phenyl or 8-cycloalkylxanthine, and xanthine derivatives having a substituent group at the 8-position, which are represented by the formula:

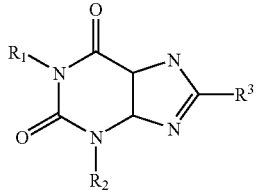

wherein 1) $R_1$ represents a hydrogen, an alkyl group, a cycloalkyl group or an aryl group; $R_2$ represents a cycloalkyl group or an aryl group; and $R_3$ represents a phenyl group, a cycloalkyl group, a phenyl group having a substituent group or a cycloalkyl group having a substituent group, or 2) $R_1$ and $R_2$ each represents a group shown by the formula:

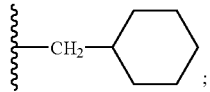

and $R_3$ represents a group shown by the formula:

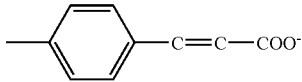

(WO9942093)

(13) 1) 3-n-Propylxanthine; 2) 1,3-dipropyl-8-(p-acrylic) phenylxanthine; 3) 1,3-dipropyl-8-cyclopentylxanthine; 4) 1,3-dipropyl-8-(p-sulfophenyl)xanthine; 5) xanthinamine analogues; 6) 1,3-dipropyl-8-[2-(5,6-epoxynorbonyl)]xanthine; and 7) 1,3-dimethylcyclohexyl-8-phenyl(4-acrylate) xanthine (U.S. Pat. No. 6,060,481)

(14) Substituted 8-phenylxanthine derivative I represented by the formula:

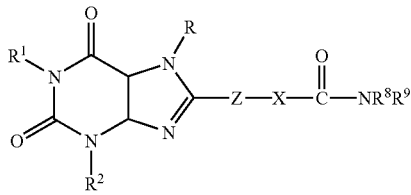

(wherein R and $R^1$ independently represent hydrogen, ($C_1$ to $C_8$) alkyl, ($C_2$ to $C_8$) alkenyl, ($C_2$ to $C_8$) alkynyl, ($C_1$ to $C_8$) alkoxy, ($C_3$ to $C_8$) cycloalkyl, ($C_4$ to $C_{16}$) cycloalkyl alkyl, a heterring, ($C_6$ to $C_{10}$) aryl, ($C_7$ to $C_{18}$) aralkyl or heteroaryl;

Z means a group represented by:

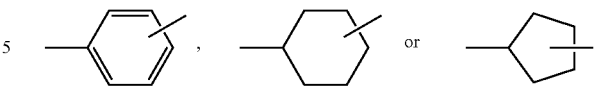

X represents ($C_1$ to $C_8$) alkylene, ($C_2$ to $C_8$) alkenylene and ($C_2$ to $C_8$) alkynylene, and one carbon atom of the alkylene, alkenylene or alkynylene may be substituted with a substituent group containing —O—, —N($R^4$)C(O)—, —OC(O)—, —N($R^5$) ($R^6$)—, —S—, —S(O)— or —SO$_2$—;

$R^2$ represents hydrogen, ($C_1$ to $C_8$) alkyl, ($C_2$ to $C_8$) alkenyl, ($C_2$ to $C_8$) alkynyl, ($C_1$ to $C_8$) alkoxy, ($C_3$ to $C_8$) cycloalkyl, ($C_4$ to $C_{16}$) cycloalkyl alkyl, ($C_6$ to $C_{10}$) aryl, ($C_7$ to $C_{18}$) aralkyl, a heterring or heteroaryl, and $R^2$ may be substituted with one or more substituent groups selected from the group consisting of substituent groups containing —OH, —SH, —NH$_2$, —NHR$^7$, —CN, —COOH and —SO$_3$H;

$R^4$, $R^5$, $R^6$ and $R^7$ independently represent hydrogen, ($C_1$ to $C_8$) alkyl, ($C_2$ to $C_8$) alkenyl, ($C_3$ to $C_8$) cycloalkyl, ($C_6$ to $C_{10}$) aryl, ($C_7$ to $C_{18}$) aralkyl or hetero-($C_1$ to $C_6$) alkyl;

$R^8$ represents hydrogen, ($C_3$ to $C_8$) cycloalkyl, ($C_4$ to $C_{16}$) cycloalkyl alkyl, ($C_7$ to $C_{18}$) aralkyl, a heterring or heteroaryl, each of which may be substituted with one or more substituent groups which are independently selected from oxo, ($C_1$ to $C_8$) alkyl, halo($C_1$ to $C_6$) alkyl, ($C_2$ to $C_8$) alkenyl, ($C_6$ to $C_{10}$) aryl, ($C_7$ to $C_{18}$) aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H, or $R^8$ represents ($C_1$ to $C_8$) alkyl which is substituted with one or more substituent groups which are selected independently from oxo, ($C_2$ to $C_8$) alkenyl, ($C_6$ to $C_{10}$) aryl, ($C_7$ to $C_{18}$) aralkyl, heteroaryl, —OR$^{15}$, halo, —CN, —NO$_2$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H, or $R^8$ represents ($C_6$ to $C_{10}$) aryl which is substituted with one or more substituent groups which are selected independently from ($C_1$ to $C_8$) alkyl, halo($C_1$ to $C_6$) alkyl, ($C_2$ to $C_8$) alkenyl, ($C_7$ to $C_{18}$) aralkyl, heteroaryl, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H;

$R^9$ represents —NR$^{10}$R$^{13}$, or ($C_3$ to $C_8$) cycloalkyl, ($C_4$ to $C_{16}$) cycloalkyl alkyl, ($C_7$ to $C_{18}$) aralkyl, a heterring or heteroaryl, which may be substituted with one or more substituent groups selected independently from oxo, ($C_1$ to $C_8$) alkyl, halo($C_1$ to $C_6$) alkyl, ($C_2$ to $C_8$) alkenyl, ($C_6$ to $C_{10}$) aryl, ($C_7$ to $C_{18}$) aralkyl, heteroaryl, —OR$^{15}$, halo, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H, or $R^9$ represents ($C_1$ to $C_8$) alkyl which is substituted with one or more substituent groups which are selected independently from oxo, ($C_2$ to $C_8$) alkenyl, ($C_6$ to $C_{10}$) aryl, ($C_7$ to $C_{18}$) aralkyl, heteroaryl, —OR$^{15}$, halo, —CN, —NO$_2$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H, or $R^9$ represents ($C_6$ to $C_{10}$) aryl which is substituted with one or more substituent groups which are selected independently from ($C_1$ to $C_8$) alkyl, halo($C_1$ to $C_6$) alkyl, ($C_2$ to $C_8$) alkenyl, ($C_7$ to $C_{18}$) aralkyl, heteroaryl, —OR$^{15}$, —CN, —NO$_2$, —CO$_2$R$^{15}$, —OC(O)

$R^{16}$, —C(O)$R^{16}$, —$NR^{13}R^{14}$, —$N(R^{23})C(O)R^{24}$, —C(O)$NR^{17}R^{18}$, —$SR^{19}$, —$SO_2R^{20}$ or —$SO_3H$;

$R^{10}$ and $R^{11}$ independently represent halogen, ($C_1$ to $C_8$) alkyl, ($C_2$ to $C_8$) alkenyl, ($C_3$ to $C_8$) cycloalkyl, ($C_6$ to $C_{10}$) aryl, ($C_7$ to $C_{18}$) aralkyl, a heteroring, heteroaryl, —C(O)$(CH_2)_nCO_2R^{12}$, —C(O)$R^{21}$=$CR^{22}(CH_2)_mCO_2R^{12}$, —C(O)$R^{12}$, —C(O) ($C_3$ to $C_8$) cycloalkyl or —C(O) ($C_3$ to $C_8$) cycloalkenyl, each of which may be substituted with one or more substituent groups which are independently selected from oxo, ($C_1$ to $C_8$) alkyl, halo($C_1$ to $C_6$) alkyl, ($C_2$ to $C_8$) alkenyl, ($C_6$ to $C_{10}$) aryl, ($C_7$ to $C_{18}$) aralkyl, heteroaryl, —$OR^{15}$, halo, —CN, —$NO_2$, —$CO_2R^{15}$, —OC(O)$R^{16}$, —C(O)$R^{16}$, —$NR^{13}R^{14}$, —$N(R^{23})C(O)R^{24}$, —C(O)$NR^{17}R^{18}$, —$SR^{19}$, —$SO_2R^{20}$ or —$SO_3H$, or $R^{10}$ and $R^{11}$ together with a nitrogen atom may form a heteroring or heteroaryl ring, each of which may be substituted with one or more substituent groups which are independently oxo, ($C_1$ to $C_8$) alkyl, halo($C_1$ to $C_6$) alkyl, ($C_2$ to $C_8$) alkenyl, ($C_6$ to $C_{10}$) aryl, ($C_7$ to $C_{18}$) aralkyl, heteroaryl, —$OR^{15}$, halo, —CN, —$NO_2$, —$CO_2R^{15}$, —OC(O)$R^{16}$, —C(O)$R^{16}$, —$NR^{13}R^{14}$, —$N(R^{23})C(O)R^{24}$, —C(O)$NR^{17}R^{18}$, —$SR^{19}$, —$SO_2R^{20}$ or —$SO_3H$; n is 1 to 6; m is 0 to 4;

$R^{12}$ represents hydrogen, ($C_1$ to $C_8$) alkyl, ($C_2$ to $C_8$) alkenyl, ($C_2$ to $C_8$) alkynyl, ($C_3$ to $C_8$) cycloalkyl, ($C_4$ to $C_{16}$) cycloalkyl alkyl, ($C_6$ to $C_{10}$) aryl, ($C_7$ to $C_{18}$) aralkyl, a heteroring or heteroaryl;

$R^{12}$ may be substituted with one or more substituent groups which are independently selected from oxo, ($C_1$ to $C_8$) alkyl, halo($C_1$ to $C_6$) alkyl, ($C_2$ to $C_8$) alkenyl, ($C_6$ to $C_{10}$) aryl, ($C_7$ to $C_{18}$) aralkyl, heteroaryl, —$OR^{15}$, halo, —CN, —$NO_2$, —$CO_2R^{15}$, —OC(O)$R^{16}$, —C(O)$R^{16}$, —$NR^{13}R^{14}$, —$N(R^{23})C(O)R^{24}$, —C(O)$NR^{17}R^{18}$, —$SR^{19}$, —$SO_2R^{20}$ or —$SO_3H$;

$R^{13}$, $R^{14}$, $R^{15}$, $R^{16}$, $R^{17}$, $R^{18}$, $R^{19}$, $R^{20}$, $R^{23}$ and $R^{24}$ independently represent hydrogen, ($C_1$ to $C_8$) alkyl, ($C_2$ to $C_8$) alkenyl, ($C_3$ to $C_8$) cycloalkyl, ($C_6$ to $C_{10}$) aryl, ($C_7$ to $C_{18}$) aralkyl or halo($C_1$ to $C_6$) alkyl; and $R^{21}$ and $R^{22}$ independently represent hydrogen, ($C_1$ to $C_8$) alkyl, ($C_2$ to $C_8$) alkenyl, ($C_3$ to $C_8$) cycloalkyl, ($C_6$ to $C_{10}$) aryl or ($C_7$ to $C_{18}$) aralkyl, provided that when —$NR^8R^9$ is not aminoalkyl, aminodialkyl or hydradino, or both R and $R^8$ are hydrogen and both $R^1$ and $R^2$ are alkyl, $R^9$ is not 2-hydroxyethyl, 2-thiolethyl, 2-haloethyl, 2,2-dimethoxyethyl, 2-acetoxyethyl, 1-methyl-2-phenylethyl, 4-methylphenyl or 4-hydroxyphenyl) or a pharmacologically acceptable salt thereof (WO 0073307).

(15) Aryl pyridinylthiazole derivatives represented by the formula:

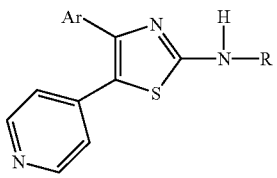

(wherein Ar represents an unsubstituted or substituted aryl group which bound via a carbon atom of the aromatic ring thereof to a carbon atom of the thiazole shown in the formula; and R represents a hydrogen, an acyl group or an aromatic ring containing 10 or more carbon atoms which bound via a carbon atom of the aromatic ring thereof to the nitrogen atom shown in the formula, and when Ar is phenyl or 4-methoxyphenyl, R is not hydrogen) or a salt thereof (WO9964418).

(16) 1) 3-n-Propylxanthine; 2) 1,3-dipropyl-8-(p-acrylic) phenylxanthine; 3) 1,3-dipropyl-8-cyclopentylxanthine; 4) 1,3-dipropyl-8-(p-sulfophenyl)xanthine; 5) a xanthineamine congener; and 6) 1,3-dipropyl-8-[2-(5,6-epoxynorbonyl)] xanthine (U.S. Pat. No. 6,060,481).

(17) Compounds represented by the formulae:

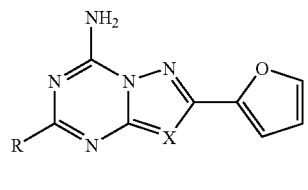

| | R | X |
|---|---|---|
| ZM241385 | 4-HO—Ph$(CH_2)_2$NH | N |
| LUF5441 | 4-HO—Ph$(CH_2)_2$NH | CH |
| LUF5443 | MeS | N |
| LUF5452 | Ph$(CH_2)_2$NH | N |
| LUF5451 | Bn—NH | N |
| LUF5453 | Ph—NH | N |
| LUF5478 | Ph$(CH_2)_3$NH | N |
| LUF5455 | 4-Cl—Bn—NH | N |
| LUF5456 | 3-Cl—Bn—NH | N |
| LUF5457 | 3,4-di-Cl—Bn—NH | N |
| LUF5458 | 4-MeO—Bn—NH | N |
| LUF5459 | 4-Me—Bn—NH | N |
| LUF5460 | (R)-α-Me—Bn—NH | N |
| LUF5461 | (S)-α-Me—Bn—NH | N |
| LUF5479 | $(Ph)_2$CHNH | N |
| LUF5462 | (Bn)$(CH_3)$N | N |
| LUF5475 | PhNHNH | N |
| LUF5477 | Cyclohexyl-$CH_2$NH | N |

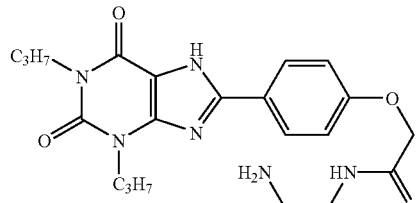

XAC

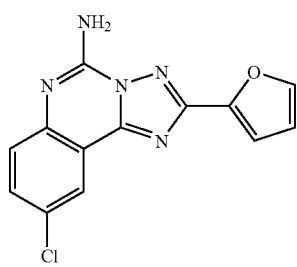

CGS15943

(Drug Development Research 48: 95–103 (1999)).

(18) Compounds represented by the formulae:

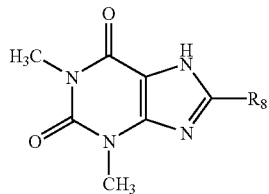

R₈ = H (theophylline)
R₈ = CH₂-cyclohexyl
R₈ = cycloheptyl

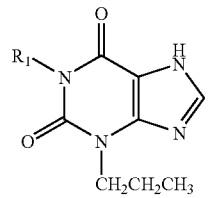

R₁ = H (enprofylline)
R₁ = CH₃
R₁ = CH₂CH₂CH₃ (dipropylxanthine)

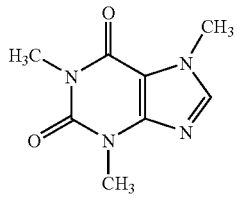

caffeine

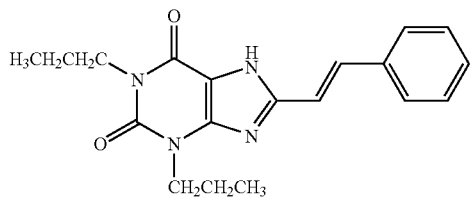

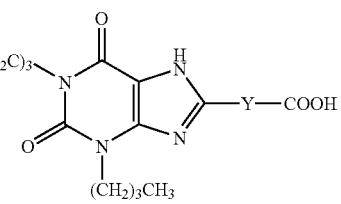

Y = CH₂ = CH₂ (trans)
Y = (CH₂)₃

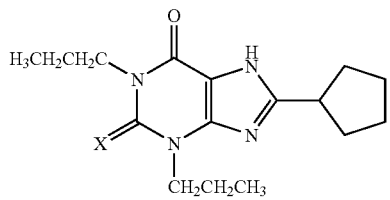

X = O (CPX)
X = S (2-thioCPX)

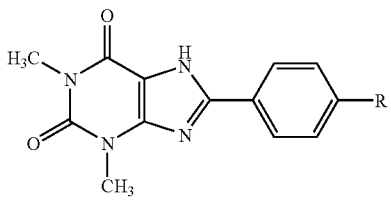

R = H (8-phenyltheophylline)
R = SO₃H
(8-p-sulfophenyltheophylline)

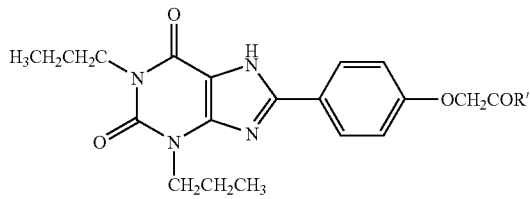

R' = OH (XCC)
R' = NH—NH₂
R' = NH—(CH₂)₂—OH
R' = NH—(CH₂)₂—F
R' = NH—(CH₂)₂—NH₂ (XAC)
R' = NH—(CH₂)₂—N(CH₃)₂
R' = NH—(CH₂)₂—NHCOCH₃

R' = NH—(CH₂)₂—NH—(CH₂)₂—OH
R' = NH—(CH₂)₈—NH₂
R' = Biotin-NH—(CH₂)₂—NH
R' = Biotin-NH—CH₂—CO—NH—(CH₂)₂—NH
R' = Biotin-NH—(CH₂)₅—CO—NH—(CH₂)₂—NH

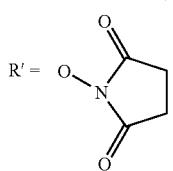

R' =

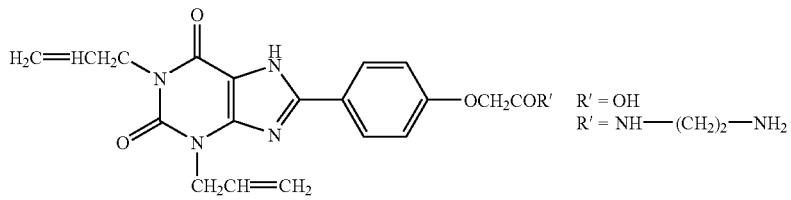

OCH₂COR'    R' = OH
R' = NH—(CH₂)₂—NH₂

-continued

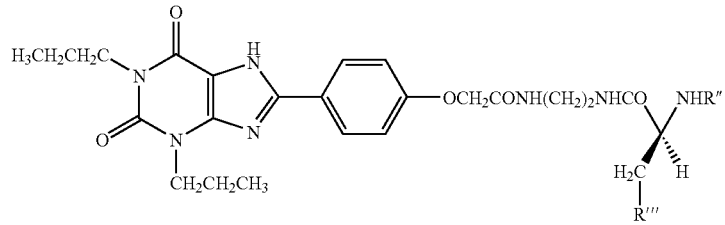

R″ = H, R‴ = CH₂CONH₂
R″ = H, R‴ = (CH₂)₂NHCONH₂

R″ = COOC(CH₃)₃, R‴ = CH₂SCH₃
R″ = COOC(CH₃)₃, R‴ = CH₂CONH₂
R″ = COOC(CH₃)₃,
R‴ = (CH₂)₂NHCONH₂

R″ = H, R‴ = 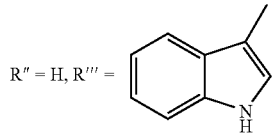

R″ = COOC(CH₃)₃, R‴ = 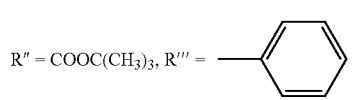

R″ = H, R‴ = 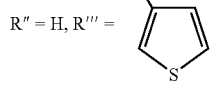

R″ = COOC(CH₃)₃, R‴ = 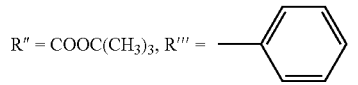

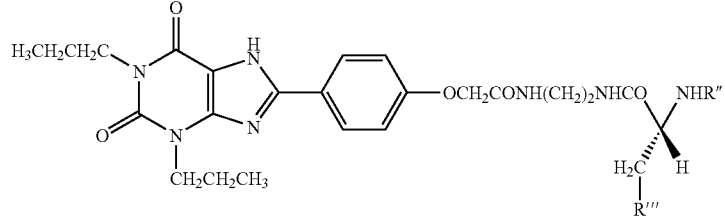

R″ = COOC(CH₃)₃,
R‴ = (CH₂)₄NH₂
R″ = H, R‴ = p-NH₂-phenyl (Drug Development Research 47: 45–53 (1999)).

(19) Compounds represented by the formula:

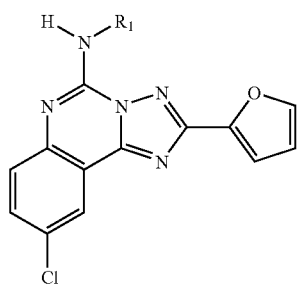

R₁═H, COCH₂—Ph, CH₂—Ph, COCH₂(4-NH₂-3-I—Ph),
COCH₂(4-NH₂—Ph),
COCH₂-(4-I—Ph), COCH₂-(3-Cl—Ph), COCH₂CH₂—Ph,
COCH═CH—Ph,
CO(CH₂)₃—NH—Boc, CO(CH₂)₂—NH₂, CO(CH₂)₃—NH₂,
CO(CH₂)₄—NH₂,
CO(CH₂)₅—NH₂, CO(CH₂)₆—NH₂, CO(CH₂)₃—COOH, COOH₃,
COCH₂CH₃,
CO(CH₂)₂CH₃, CO(CH₂)₃CH₃, COC(CH₃)₃, CO—OC(CH₃)₃, CO—Ph,
CO-(3-I—PH)

(Journal of Medicinal Chemistry, 41, 2835–2845 (1998)).

(20) Compounds represented by the formula:

TABLE 7

| R₁ | X | R₂ |
|---|---|---|
| n-Pr | OCH₂ | OH |
| n-Pr | OCH₂ | O-succinimide |
| n-Pr | OCH₂ | NHN-dimethylmaleyl |
| n-Pr | OCH₂ | NH(CH₂)₂NH₂ |
| allyl | OCH₂ | OH |
| n-butyl | OCH₂ | OH |
| Bn | OCH₂ | OH |
| n-Pr | CH═CH | OH |
| c-HexMe | CH═CH | OH |
| Bn | CH═CH | OH |
| n-Pr | OCH₂ | NH₂ |
| n-Pr | OCH₂ | NH—Ph |
| n-Pr | OCH₂ | NH—CH₂Ph |
| n-Pr | OCH₂ | NH—CH(Ph)₂ |
| n-Pr | OCH₂ | N(CH₂Ph)₂ |
| n-Pr | OCH₂ | N(CH₃)Ph |
| n-Pr | OCH₂ | N(CH₂COOEt)₂ |

TABLE 7-continued

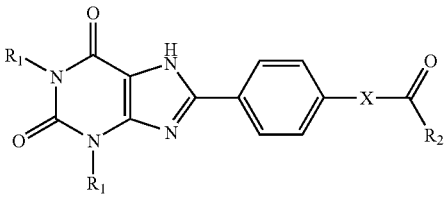

| R₁ | X | R₂ |
|---|---|---|
| n-Pr | OCH₂ | NH—Ph(2-COCH₃) |
| n-Pr | OCH₂ | NH—Ph(3-COCH₃) |
| n-Pr | OCH₂ | NH—Ph(4-COCH₃) |
| n-Pr | OCH₂ | NH—Ph(4-COOCH₃) |
| n-Pr | OCH₂ | NH—Ph(4-CONH₂) |
| n-Pr | OCH₂ | NH—Ph(4-CONHCH₃) |
| n-Pr | OCH₂ | NH—Ph(4-COOH) |
| n-Pr | OCH₂ | NH—Ph(4-CH₃) |
| n-Pr | OCH₂ | NH—Ph(4-OH) |
| n-Pr | OCH₂ | NH—Ph(4-CN) |
| n-Pr | OCH₂ | NH—Ph(4-NO₂) |
| n-Pr | OCH₂ | NH—Ph(4-CF₃) |
| n-Pr | OCH₂ | NH—Ph(4-F) |
| n-Pr | OCH₂ | NH—Ph(4-Cl) |
| n-Pr | OCH₂ | NH—Ph(4-Br) |
| n-Pr | OCH₂ | NH—Ph(4-I) |
| n-Pr | CH=CH | NHN-dimethylmaleyl |
| n-Pr | CH=CH | NH—Ph(2-COCH₃) |
| Et | OCH₂ | NH—Ph(4-CH₃) |
| Et | OCH₂ | NH—Ph(4-CH₂CONH(CH₂)₂NH₂) |

(Journal of Medicinal Chemistry, 43, 1165–1172 (2000)).

(21) Compounds represented by the formula:

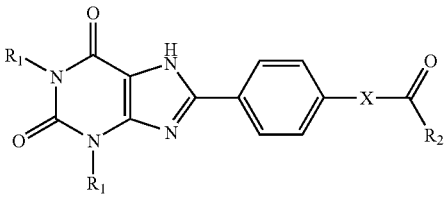

| X | Y | Z |
|---|---|---|
| H | NH₂ | Br |
| H | NH₂ | O—(CH₂)₂—C₆H₅ |
| H | NH₂ | C≡C—(CH₂)₃—CH₃ |
| O—(CH₂)₂—C₆H₅ | NH₂ | H |
| NH—(CH₂)₂—C₆H₅ | NH₂ | H |
| C≡C—(CH₂)₃—CH₃ | NH₂ | H |
| H | NH—(CH₂)₂—C₆H₅ | H |
| H | C≡C—(CH₂)₂—C₆H₅ | H |
| H | NH—(CH₂)₂—C₆H₅ | Br |

(Bioorganic & Medicinal Chemistry, 6, 523–533 (1998)).

(22) Compounds represented by the formulae:

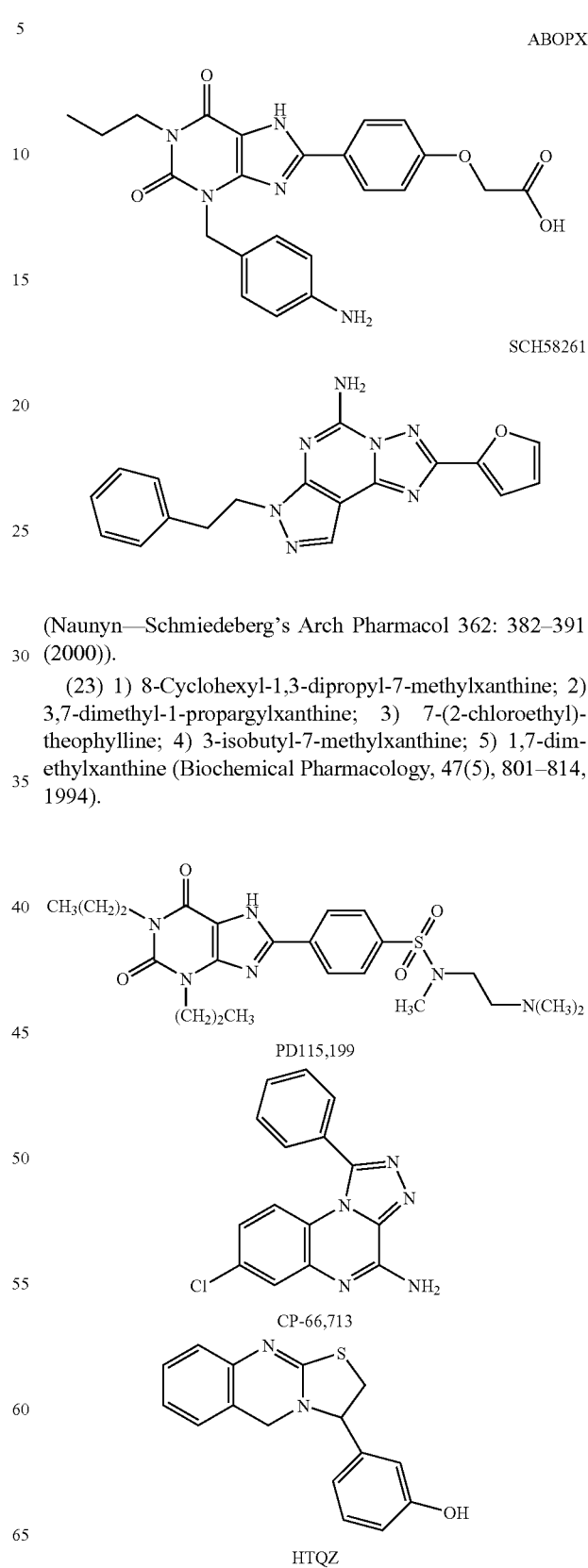

(Naunyn—Schmiedeberg's Arch Pharmacol 362: 382–391 (2000)).

(23) 1) 8-Cyclohexyl-1,3-dipropyl-7-methylxanthine; 2) 3,7-dimethyl-1-propargylxanthine; 3) 7-(2-chloroethyl)-theophylline; 4) 3-isobutyl-7-methylxanthine; 5) 1,7-dimethylxanthine (Biochemical Pharmacology, 47(5), 801–814, 1994).

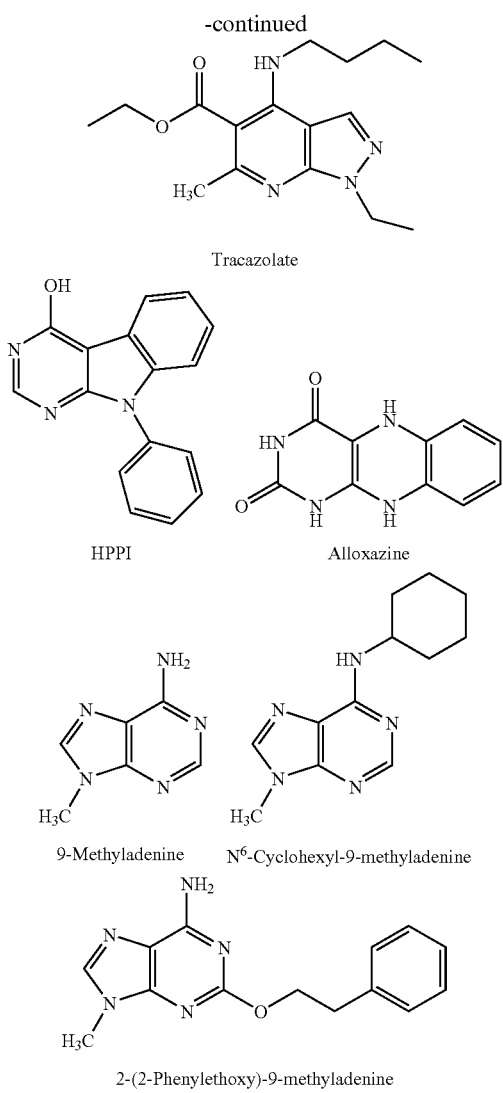

Tracazolate

HPPI

Alloxazine

9-Methyladenine

N⁶-Cyclohexyl-9-methyladenine 2-(2-Phenylethoxy)-9-methyladenine

(24) 1) 8-FB-PTP (5-amino-8-(4-fluorobenzyl)-2-(2-furyl)-pyrazolo[4,3-e]-1,2,4-triazolo[1,5-c]pyrimidine); 2) 3-propylxanthine (British Journal of Pharmacology 119, 1286–1290 (1996)).

(25) Compounds represented by the formula:

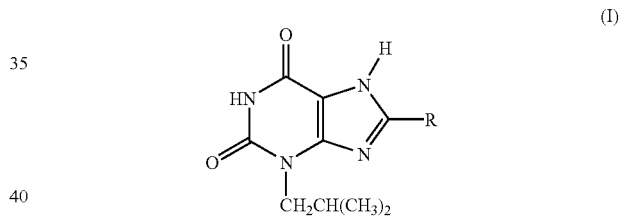

| Ar | R² |
|---|---|
| C₆H₅ | c-C₆H₁₀(OH) |
| 2-furyl | c-C₆H₁₀(OH) |
| 2-thienyl | c-C₆H₁₀(OH) |
| 2-pyridyl | c-C₆H₁₀(OH) |
| 2-FC₆H₄ | c-C₆H₁₀(OH) |
| 3-FC₆H₄ | c-C₆H₁₀(OH) |
| 4-FC₆H₄ | c-C₆H₁₀(OH) |
| 3-ClC₆H₄ | c-C₆H₁₀(OH) |
| 4-ClC₆H₄ | c-C₆H₁₀(OH) |
| 3-(CN)C₆H₄ | c-C₆H₁₀(OH) |
| 3-MeC₆H₄ | c-C₆H₁₀(OH) |
| 3-MeOC₆H₄ | c-C₆H₁₀(OH) |
| 3-FC₆H₄ | c-C₅H₈(OH) |
| 3-FC₆H₄ | c-C₇H₁₂(OH) |
| 3-FC₆H₄ | (CH₃)₂(OH)C |
| 3-FC₆H₄ | (C₂H₅)₂(OH)C |
| 3-FC₆H₄ | c-C₅H₉ |
| H | c-C₆H₁₀(OH) |

(Journal of Medicinal Chemistry 44, 170–179 (2001)).

(26) 1) 1-Methylxanthine; 2) 3-methylxanthine; 3) 7-methylxanthine; 4) 3-isobutyl-1-methylxanthine; 5) 1,3-dimethyl-8-cyclopentylxanthine (Pharmaceutica Acta Helvetiae 68, 77–111 (1993)).

(27) Compounds represented by the formula:

$$\text{(I)}$$

wherein R represents an aliphatic or alicyclic amino group (for example a $C_1$ to $C_6$ alkylamino group, a $C_1$ to $C_6$ dialkylamino group, a piperidino group, a piperazino group, a pyrrolidino group, a pyrrolino group, a morpholino, or an aminocyclohexyl derivative (WO 01/16134).

For example, the defecation-promoting actions of 8-phenyltheophylline ("8-PT" in the table below) and 5-[6-amino-8-(3-fluorophenyl)-9H-9-purinyl]-1-methyl-1,2-dihydro-2-pyridinone (Compound II in the table below) disclosed in Example Number 5 described in WO 2001/2400 were as shown below. 8-PT can be easily produced according to the description of Drug Development Research 47: 45–53 (1999), or is easily available as a commercial product (in this test, it was purchased from Sigma).

TABLE 8

| Compound | Dose | The number of fecal pellets/3 rats | |
|---|---|---|---|
| Control | — | 3.25 ± 2.02 | |
| 8-PT | 3 mg/kg | 8.75 ± 1.75 | NS |
| | 10 mg/kg | 13.75 ± 0.85 | ** |
| Compound I | 3 mg/kg | 20.75 ± 3.15 | *** |
| Control | — | 2.5 ± 0.87 | |

TABLE 8-continued

| Compound | Dose | The number of fecal pellets/3 rats | |
|---|---|---|---|
| Compound II | 1 mg/kg | 12.5 ± 1.44 | ** |
| | 3 mg/kg | 18.5 ± 1.94 | *** |
| | 10 mg/kg | 20.75 ± 1.70 | *** |
| Compound I | 3 mg/kg | 19.75 ± 2.50 | *** |

The number of cages; n = 4 cages/group (12 rats/group)
p < 0.01, *p < 0.001, Dunnett's test The present invention also relates to a compound represented by the above formula (I) or (II) or a salt of them. The compound is a novel pyrimidine compound found in the process of searching for the defecation-promoting pharmaceutical composition according to the present invention. The compound is a compound exhibiting an excellent antagonistic action on adenosine $A_2$ receptor, particularly on adenosine $A_{2b}$ receptor and having an excellent defecation-promoting action.

The structural formulae of the compounds represented by the formula (I) or (II) in the present invention or a salt thereof may, for convenience' sake, indicate a certain isomer, but this invention encompasses all possible isomers which can occur in the structures of the compounds, for example geometric isomer, optical isomer based on asymmetrical carbon, stereoisomer and tautomer, as well as a mixture of such isomers, so the compound of the invention may be any isomers or a mixture thereof without limitation to the formulae shown for convenience' sake. Compound (I) or (II) can have an intramolecular asymmetrical carbon to occur as optically active isomers or racemic modifications, and any of such compounds are included in this invention without limitation. When there is crystal polymorphism, the compound of the invention may be in a single crystal form or a mixed crystal form without limitation. Compound (I) or (II) in the invention or salts thereof may be anhydrides or hydrates, any of which fall under the claims in this specification. Further, metabolites formed by decomposition of Compound (I) or (II) in the living body, as well as prodrugs of Compound (I) or (II) or salts thereof, also fall under the claims in this specification.

The "halogen atom" used in this specification refers to an atom such as, for example, a fluorine atom, a chlorine atom, a bromine atom or an iodine atom, preferably a fluorine atom, a chlorine atom or a bromine atom, more preferably a fluorine atom or a chlorine atom, still more preferably a fluorine atom.

The "$C_{1-6}$ alkyl group" used in this specification refers to an alkyl group containing 1 to 6 carbon groups, and examples thereof include linear or branched alkyl groups, preferably a methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1,-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group etc., more preferably a methyl group, ethyl group, n-propyl group, iso-propyl group, n-butyl group, iso-butyl group, sec-butyl group, tert-butyl group, n-pentyl group etc.

The "$C_{1-6}$ alkoxy group" used in this specification refers to an alkoxy group containing 1 to 6 carbon groups, and preferable examples include e.g. a methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethyl propoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, hexyloxy group etc.

The "$C_{1-6}$ alkoxy-carbonyl group" used in this specification refers to a carbonyl group to which a $C_{1-6}$ alkoxy group was bound, and examples thereof include a methoxycarbonyl group, ethoxycarbonyl group, n-propoxycarbonyl group, iso-propoxycarbonyl group, sec-propoxycarbonyl group, n-butoxycarbonyl group, iso-butoxycarbonyl group, sec-butoxycarbonyl group, tert-butoxycarbonyl group, n-pentyloxycarbonyl group, iso-pentyloxycarbonyl group, sec-pentyloxycarbonyl group, n-hexoxycarbonyl group, iso-hexoxycarbonyl group, 1,1-dimethylpropyloxycarbonyl group, 1,2-dimethylpropoxycarbonyl group, 2,2-dimethylpropoxycarbonyl group, 2-ethylpropoxycarbonyl group, 1-methyl-2-ethylpropoxycarbonyl group, 1-ethyl-2-methylpropoxycarbonyl group, 1,1,2-trimethylpropoxycarbonyl group, 1,1,2-trimethylpropoxycarbonyl group, 1,1-dimethylbutoxycarbonyl group, 1,2-dimethylbutoxycarbonyl group, 2,2-dimethylbutoxycarbonyl group, 2,3-dimethylbutyloxycarbonyl group, 1,3 -dimethylbutyloxycarbonyl group, 2-ethylbutoxycarbonyl group, 1,3-dimethylbutoxycarbonyl group, 2-methylpentoxycarbonyl group, 3-methylpentoxycarbonyl group, hexyloxycarbonyl group etc.

The "acyl group" used in this specification refers to an atomic group derived from a $C_{1-7}$ fatty acid carboxyl group by removing its OH group, and preferable groups include e.g. an acetyl group, propionyl group, butyroyl group etc.

The "$C_{1-6}$ alkyl sulfonyl group" used in this specification refers to a sulfonyl group to which a $C_{1-6}$ alkyl group was bound, and preferable groups include a methylsulfonyl group, ethylsulfonyl group, n-propylsulfonyl group, iso-propylsulfonyl group, n-butylsulfonyl group, iso-butylsulfonyl group, sec-butylsulfonyl group, tert-butylsulfonyl group, n-pentylsulfonyl group, n-hexylsulfonyl group etc.

In the formula. (I) or (II), A represents a phenyl group, a pyridyl group, a thienyl group or a furyl group which may be substituted with one or two groups selected from a halogen atom, a hydroxyl group, a $C_{1-6}$ alkyl group, a $C_{1-6}$ alkoxy group and a $C_{1-6}$ alkoxy-carbonyl group, and preferable examples of the group A are not particularly limited. More preferable examples of the group A include a phenyl group, a pyridyl group, a thienyl group and a furyl group, each of which may be substituted with one to three groups selected from a fluorine atom, a chlorine atom, a hydroxyl group, a methyl group, an ethyl group, a methoxy group and an ethoxy group. Still more preferable groups include 1) a phenyl group, 2-pyridyl group, 3-pyridyl group, 4-pyridyl group, 2-furyl group, 3-furyl group, 2-thienyl group and 3-thienyl group, each of which is unsubstituted, and 2) a phenyl group, 2-pyridyl group, 3-pyridyl group, 4-pyridyl group, 2-furyl group, 3-furyl group, 2-thienyl group, 3-thienyl group etc., each of which is substituted with one to three groups selected from a fluorine atom, chlorine atom, hydroxyl group, methyl group, ethyl group, methoxy group and ethoxy group.

In the formula (I), B represents a pyridyl group which may be substituted with one or more groups selected from a halogen atom, a hydroxyl group, a $C_{1-6}$ alkyl group and an amino group, and preferable examples of the group B are not particularly limited. More preferable examples of the group B is 1) an unsubstituted 4-pyridyl group or 2) a 4-pyridyl group which is substituted with one to three groups selected from a fluorine atom, a chlorine atom, a hydroxyl group, a methyl group, an ethyl group, a n-propyl group, an iso-propyl group and an amino group.

In the formula (II), B' represents a 1,2-dihydro-2-pyridinone-4-yl group which may be substituted with one or more groups selected from a halogen atom, a hydroxyl group, a $C_{1-6}$ alkyl group and an amino group, and preferable examples of the group B' are not particularly limited, and more preferable examples include 1) an unsubstituted 1,2-dihydro-2-pyridinone-4-yl group, 2) an 1,2-dihydro-2-pyridinone-4-yl group which is substituted with one to two groups selected from a fluorine atom, chlorine atom, hydroxyl group, methyl group, ethyl group, n-propyl group, iso-propyl group and amino group, and a still further preferable group is an unsubstituted 1,2-dihydro-2-pyridinone-4-yl group.

In the above formula (I) or (II), $R^1$ represents a hydrogen atom, a morpholinyl group, or a group represented by the formula —$NR^{1a}R^{1b}$ (wherein $R^{1a}$ and $R^{1b}$ are the same as or different from each other and each represents a hydrogen atom, a $C_{1-6}$ alkyl group, a $C_{1-6}$ acyl group, a phenyl group or a $C_{1-6}$ alkyl sulfonyl group), and 1) a hydrogen atom, 2) a 4-morpholinyl group, 3) an amino group, 4) a $C_{1-6}$ alkylamino group (for example, a methylamino group, ethylamino group, n-propylamino group, iso-propylamino group etc.), 5) an N,N-di$C_{1-6}$ alkyl amino group (for example, a dimethylamino group, diethylamino group, etc.), 6) a $C_{1-6}$acyl amino group (for example, an acetamide group, propionylamino group, etc.), 7) an N,N—$C_{1-6}$ alkyl ($C_{1-6}$ acyl) amino group and 8) a $C_{1-6}$ alkylsulfonylamino group (for example, a methylsulfonylamino group, an ethylsulfonylamino group, a n-propylsulfonylamino group, an iso-propylsulfonylamino group, etc.) are more preferable.

In the formula (I) or (II), $R^2$ represents a hydrogen atom or a group represented by the formula —$NR^{2a}R^{2b}$ (wherein $R^{2a}$ and $R^{2b}$ are the same as or different from each other and each represents a hydrogen atom or a $C_{1-6}$ alkyl group, and more preferable groups include a hydrogen atom, an amino group, a methyl amino group, an ethyl amino group, an N,N-dimethylamino group, an N,N-methylethylamino group, etc.

Preferable examples of Compound (I) or (II) include the following compounds:
 6-(3-flurophenyl)-5-(4-pyridyl)-2,4-pyrimidinediamine; 6-(2-furyl)-5-(4-pyridyl)-2,4-pyrimidinediamine; 4-(2-furyl)-5-(4-pyridyl)-2-pyrimidinylamine; 4-(3-fluorophenyl)-5-(4-pyridyl)-2-pyrimidinylamine; 4-phenyl-5-(4-pyridyl)-2-pyrimidinylamine; 5-(4-pyridyl)-4-(2-thienyl)-2-pyrimidinylamine; 4-(2-pyridyl)-5-(4-pyridyl)-2-pyrimidinylamine; 4-(3-fluorophenyl)-5-(4-pyridyl) pyrimidine; 4-(3-fluorophenyl)-5-(2-fluoro-4-pyridyl) pyrimidine; 4-(3-fluorophenyl)-5-(2-fluoro-4-pyridyl)-2-pyrimidinylamine; N-[4-(3-fluorophenyl)-5-(4-pyridyl)-2-pyrimidinyl]-N,N-dimethylamine; N-[4-(3-fluorophenyl)-5-(4-pyridyl)-2-pyrimidinyl]-N-methylamine; 4-[4-(3-fluorophenyl)-5-(4-pyridyl)-2-pyrimidinyl]morpholine; N-[4-(3-fluorophenyl)-5-(2-fluoro-4-pyridyl)-2-pyrimidinyl]-N-methylamine; 4-[4-(3-fluorophenyl)-2-(methylamino)-5-pyrimidinyl]-1,2-dihydro-2-pyridinone; N-ethyl-N-[4-(3-fluorophenyl)-5-(4-pyridyl)-2-pyrimidinyl]amine; N1-[4-(3-fluorophenyl)-5-(4-pyridyl)-2-pyrimidinyl]acetamide; N1-[4-(3-fluorophenyl)-5-(4-pyridyl)-2-pyrimidinyl]-N1-methylacetamide; N1-[4-(3-fluorophenyl)-5-(4-pyridyl)-2-pyrimidinyl]propanamide; N1-[4-(3-fluorophenyl)-5-(4-pyridyl)-2-pyrimidinyl]butanamide; N1-[4-(3-fluorophenyl)-5-(4-pyridyl)-2-pyrimidinyl]-N1-methylpropanamide; 4-(3-fluorophenyl)-5-(2-methyl-4-pyridyl)-2-pyrimidinylamine; N1-ethyl-N1-[4-(3-fluorophenyl)-5-(4-pyridyl)-2-pyrimidinyl]propanamide; N1-[4-(3-fluorophenyl)-5-(2-fluoro-4-pyridyl)-2-pyrimidinyl]propanamide; N1-[4-(3-fluorophenyl)-5-(2-methyl-4-pyridyl)-2-pyrimidinyl]propanamide; 4-[2-amino-4-(3-fluorophenyl)-5-pyrimidinyl]-1,2-dihydro-2-pyridinone; N-ethyl-N-[4-(3-fluorophenyl)-5-(2-fluoro-4-pyridyl)-2-pyrimidinyl]amine; 4-[2-(ethylamino)-4-(3-fluorophenyl)-5-pyrimidinyl]-1,2-dihydro-2-pyridinone; N-[4-(3-fluorophenyl)-5-(4-pyridyl)-2-pyrimidinyl]-N-propylamine; N-[4-(3-fluorophenyl)-5-(4-pyridyl)-2-pyrimidinyl]-N-phenylamine; N-ethyl-N-[4-(3-fluorophenyl)-5-(2-methyl-4-pyridyl)-2-pyrimidinyl]amine; 5-(2,6-dimethyl-4-pyridyl)-4-(3-fluorophenyl)-2-pyrimidinylamine; N-[5-(2,6-dimethyl-4-pyridyl)-4-(3-fluorophenyl)-2-pyrimidinyl]-N-ethylamine; 4-(3-fluorophenyl)-5-(3-methyl-4-pyridyl)-2-pyrimidinylamine; 5-(3-ethyl-4-pyridyl)-4-(3-fluorophenyl)-2-pyrimidinylamine; 5-(2-amino-4-pyridyl)-4-(3-fluorophenyl)-2-pyrimidinylamine; N4-methyl-6-(3-fluorophenyl)-5-(4-pyridyl)-2,4-pyrimidinediamine; N4,N4-dimethyl-6-(3-fluorophenyl)-5-(4-pyridyl)-2,4-pyrimidinediamine; N-ethyl-N-[4-(2-furyl)-5-(4-pyridyl)-2-pyrimidinyl]amine; N-ethyl-N-[4-(3-fluorophenyl)-5-(4-pyridyl)-2-pyrimidinyl]amine; N-ethyl-N-[4-phenyl-5-(4-pyridyl)-2-pyrimidinyl]amine; N-ethyl-N-[5-(4-pyridyl)-4-(2-thienyl)-2-pyrimidinyl]amine; 5-(3-ethyl-4-pyridyl)-4-(2-furyl)-2-pyrimidinyl amine; N-ethyl-N-[5-(3-ethyl-4-pyridyl)-4-(2-furyl)-2-pyrimidinyl]amine; 4-(2,5-dimethyl-3-furyl)-5-(3-ethyl-4-pyridyl)-2-pyrimidinylamine; N-[4-(2,5-dimethyl-3-furyl)-5-(3-ethyl-4-pyridyl)-2-pyrimidinyl]-N-ethylamine; 5-(2,6-dimethyl-4-pyridyl)-6-(3-fluorophenyl)-2,4-pyrimidinediamine; 4-(3-methyl-2-furyl)-5-(4-pyridyl)-2-pyrimidinylamine; N-[4-(3-fluorophenyl)-5-(4-pyridyl)-2-pyrimidinyl]methanesulfonamide; 4,5-di(4-pyridyl)-2-pyrimidinylamine; 4-(4-methoxyphenyl)-5-(4-pyridyl)-2-pyrimidinylamine; 4-(3,4-dimethoxyphenyl)-5-(4-pyridyl)-2-pyrimidinylamine; 4-[2-amino-5-(4-pyridyl)-4-pyrimidinyl]phenol; methyl 3-[2-amino-5-(4-pyridyl)-4-pyrimidinyl]benzoate; and N4, N4-dimethyl-6-(2-furyl)-5-(4-pyridyl)-2,4-pyrimidinediamine.

The compounds represented by the above formula (I) or (II) in this invention can be produced by various methods, but typical production methods are as follows. In the following production methods, "room temperature" refers usually to 10 to 35° C.

Production Method A

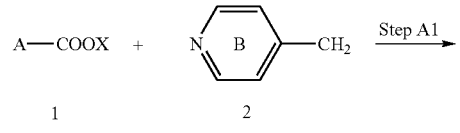

-continued

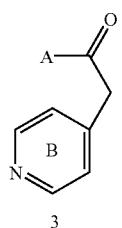

3 wherein A represents a phenyl group, pyridyl group, thienyl group or furyl group which may be substituted with one or two groups selected from a halogen atom, a hydroxyl group, a $C_{1-6}$ alkyl group, a $C_{1-6}$ alkoxy group and a $C_{1-6}$ alkoxycarbonyl group, B represents a pyridyl group which may be substituted with one or more groups selected from a halogen atom, a hydroxyl group, a $C_{1-6}$ alkyl group and an amino group, and X represents a $C_{1-8}$ alkyl group. Step $A_1$ is a step of producing 1,2-biaryl-1-ethanone compound (3) which is an intermediate for production of the compound represented by the above formula (I) in this invention. That is, Compound (3) is obtained through condensation via alcohol elimination by reacting an aromatic carboxylate (1) with 4-methylpyridine derivative (2) in a solvent in the presence of a base. The base used is varied depending on the starting materials, reagents, solvent etc. used, and is not particularly limited insofar as the reaction is not inhibited, and preferable examples of the base include secondary amine metal salts such as lithium bis(trimethylsilyl)amide and lithium diisopropylamide. The solvent used is varied depending on the starting materials and reagents used, and is not particularly limited insofar as the reaction is not inhibited and the starting materials are dissolved to a certain degree, and preferable examples of the solvent include ethers such as tetrahydrofuran, dioxane, dimethyxyethane and diethylene glycol etc. The reaction temperature is preferably −78° C. to room temperature, more preferably in the vicinity of 0° C.

Production Method B

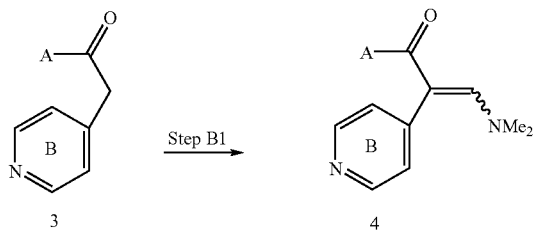

wherein A and the ring B have the same meanings as defined above; and Me is a methyl group. N,N-dimethylformamide dimethyl acetal is allowed to act on the active methylene of Compound (3) produced in Production Method A, whereby 3-(dimethylamino)-2-propene-1-one compound (4) as an intermediate for production of the compound represented by the above formula (I) in this invention can be produced (step B1) This reaction is carried out preferably in the absence of a solvent, but the reaction may be carried out after diluting with a solvent not inhibiting the reaction and dissolving the starting materials to a certain degree, for example, N,N-dimethylformamide, tetrahydrofuran, dioxane, N-methyl pyrrolidone, benzene, toluene etc. However, the solvent used herein is varied depending on the starting materials, reagents etc. used, and is not particularly limited. Usually, the reaction temperature is preferably room temperature to 120° C., more preferably about 100° C.

Production Method C

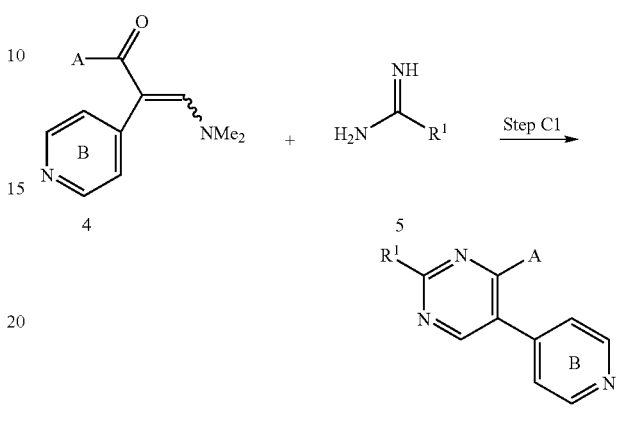

wherein A, B and Me have the same meanings as defined above, and $R^1$ represents a hydrogen atom, a morpholinyl group or a group represented by the formula —$NR^{1a}R^{1b}$ (wherein $R^{1a}$ and $R^{1b}$ are the same as or different from each other and each represents a hydrogen atom, a $C_{1-6}$ alkyl group, a $C_{1-6}$ acyl group, a phenyl group or a $C_{1-6}$ alkylsulfonyl group). Formamidine or guanidine derivative (5) is reacted in the presence of a base with the 3-(dimethylamino)-2-propene-1-one compound (4) obtained in Production Method B, whereby Compound (6) in this invention can be produced (step C1). The guanine derivative (5) used is not only easily commercially available but can also be produced by a known method described in e.g. J. Org. Chem., 57, 2497–2502 (1992) or its analogous method. The base used is varied depending on the starting materials, reagents, solvent etc. used, and is not particularly limited insofar as the reaction is not inhibited, and preferable examples include alkali metal carbonates (for example, potassium carbonate, sodium carbonate, etc.), alkali metal alkoxides (for example, sodium methoxide, sodium ethoxide, potassium tert-butoxide etc.), etc. This reaction is carried out preferably in a solvent not inhibiting the reaction and dissolving the starting materials and base to a certain degree, for example in N,N-dimethylformamide, N-methylpyrrolidone, dimethylsulfoxide, methanol, ethanol etc., but it varies depending on the starting materials, reagents etc. used, and is not particularly limited. Usually, the reaction temperature is preferably room temperature to 120° C., more preferably about 70° C.

Production Method D

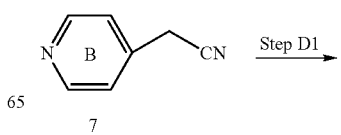

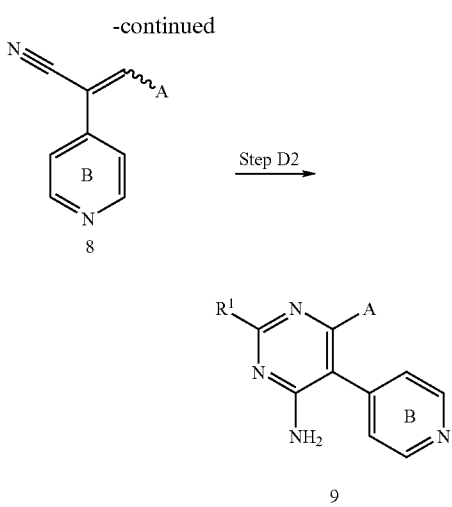

wherein A, ring B, and $R^1$ have the same meanings as defined above. Compound (9) in this invention can be obtained by dehydration condensation of aryl aldehyde with aryl acetonitrile (7) in the presence of a base, to produce 2,3-biaryl-2-propenenitrile (8) (step D1), then allowing formanidine or guanidine derivative to react on the nitrile compound (8) in the presence of a base and converting the product into an aromatic derivative by an oxidizing agent (step D2).

Step D1 The base used in step D1 is varied depending on the starting materials, reagents, solvent etc. used, and is not particularly limited insofar as the reaction is not inhibited, and preferable examples include alkali metal alkoxides (for example, sodium methoxide, sodium ethoxide, potassium tert-butoxide etc.), alkali metal carbonates (for example, potassium carbonate, sodium carbonate, etc.). The solvent used in the reaction is varied depending on the starting materials, reagents, etc. used, and is not particularly limited insofar as it dissolves the starting materials to a certain degree without inhibiting the reaction, and preferable examples include ethanol, methanol, tetrahydrofuran, dichloromethane, chloroform, N,N-dimethylformamide, N-methyl pyrrolidone, dimethylsulfoxide and mixed solvents thereof. The reaction is carried out usually at 0 to 120° C.

Step D2 The guanidine derivative used in step D2 is not only easily commercially available but can also be produced by a known method described in e.g. J. Org. Chem., 57, 2497–2502 (1992) or its analogous method. The base used is varied depending on the starting materials, reagents, solvent, etc. used, and is not particularly limited insofar as the reaction is not inhibited, and preferable examples include alkali metal alkoxides (for example, sodium methoxide, sodium ethoxide, potassium tert-butoxide, etc.), alkali metal carbonates (for example, potassium carbonate, sodium carbonate, etc.), etc. The oxidizing agent used is also varied depending on the starting materials, reagents, solvent, etc. used, and is not particularly limited insofar as the reaction is not inhibited, and preferable examples include manganese compounds (for example, activated manganese dioxide, etc.), quinones (for example, 2,3-dichloro-5,6-dicyano-1,4-benzoquinone, etc.), sulfur, etc. The solvent used is varied depending on the starting materials, reagents, etc. used, and is not particularly limited insofar as it dissolves the starting materials to a certain degree without inhibiting the reaction, and preferable examples include ethanol, methanol, tetrahydrofuran, dichloromethane, chloroform, N,N-dimethylformamide, N-methyl pyrrolidone, dimethyl sulfoxide and mixed solvents thereof. The reaction temperature in step D2 is usually 0 to 120° C.

In the step D1, the formamidine or guanidine derivative may be coexistent from the start in the reaction, and the 2,3-biaryl-2-propenenitrile (8) can be converted without isolation into its corresponding aromatic compound by an oxidizing agent, to produce the pyrimidine derivative (9) in the invention.

Production Method E

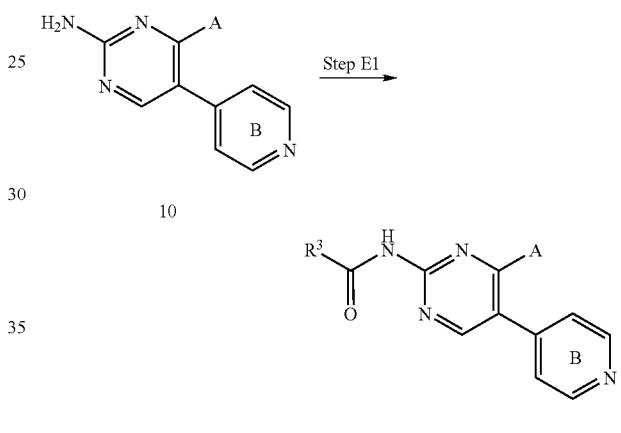

wherein A and the ring B have the same meanings as defined above, and $R^3$ represents a hydrogen atom or a $C_{1-6}$ alkyl group. Step E1 is a step where a carboxylic anhydride is allowed to act on Compound (10) under acidic conditions to acrylate the amino group thereof, whereby the acyl derivative (11) according to the present invention is produced. The starting compound (10) can be produced in Production Method C above, and corresponds to Compound (6) wherein $R^1$ is an amino group. Step E1 is carried out preferably in the absence of a solvent, but may be conducted after dilution with a solvent. Such a solvent is varied depending on the starting material, reagents, etc. used, and is not particularly limited insofar as it dissolves the staring materials without inhibiting the reaction, and preferable examples are N,N-dimethylformamide, tetrahydrofuran, dioxane, N-methyl pyrrolidone, benzene, toluene, etc. The acid used is varied depending on the starting materials, reagents, solvent, etc. used, and is not particularly limited insofar as it does not inhibit the reaction, and a preferable acid is a mineral acid such as conc. sulfuric acid. The reaction temperature is preferably room temperature to 120° C., more preferably about 90° C.

Production Method F

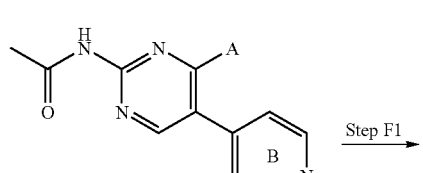

12

Step F1

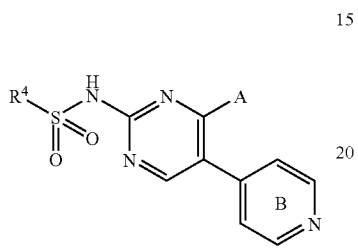

13

Production Method G

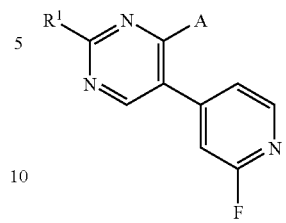

14

Step G1

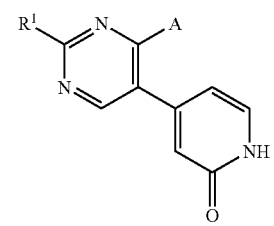

15 wherein A and the ring B have the same meanings as defined above, and $R^4$ represents a hydrogen atom or a $C_{1-6}$ alkyl group. The sulfonamide derivative (13) in this invention can be produced by allowing sulfonyl chloride under basic conditions to act on Compound (12) as the starting material (that is, Compound (11) wherein $R^3$ is a methyl group) which can be produced by Production Method E above, thus sulfonylating Compound (12), and then removing the acyl group under acidic conditions (step F1). The base used in the sulfonylation reaction is varied depending on the starting materials, reagents, solvent, etc. used, and is not particularly limited insofar as the reaction is not inhibited, and preferable examples are sodium hydride, etc. The solvent used in the sulfonylation is varied depending on the starting materials, reagents, etc. used, and is not particularly limited insofar as it dissolves the starting materials to a certain degree without inhibiting the reaction, and preferable examples include ethers such as tetrahydrofuran, dioxane, dimethyxyethane and diethylene glycol. The reaction temperature is preferably −10° C. to room temperature. The acid used in the de-acetylation reaction in step F1 is varied depending on the starting materials, reagents, solvent etc. used, and is not particularly limited insofar as the reaction is not inhibited, and a preferable example is hydrochloric acid or the like. The solvent used in the reaction is varied depending on the starting materials, reagents, etc. used, and is not particularly limited insofar as it dissolves the starting materials to a certain degree and is miscible with water to a certain degree without inhibiting the reaction, and a preferable example is a mixed solvent of an ether (for example, tetrahydrofuran) and water. The reaction temperature is preferably room temperature to 100° C.

wherein A and $R^1$ have the same meanings as defined above. The compound represented by the formula (II) in the present invention can be produced, for example, in the step G1. Compound (14) as the starting material can be produced by Production Method C above. The pyridone derivative (15) according to the present invention can be produced by hydrolyzing the according (14) under acidic conditions. The acid used is varied depending on the starting materials, reagents, solvent, etc. used, and is not particularly limited insofar as the reaction is not inhibited, and preferable examples are hydrochloric acid, hydrobromic acid, sulfuric acid, etc. This reaction is carried out preferably in water, and the reaction temperature is usually room temperature to about 120° C., preferably 100° C.

Production Method H

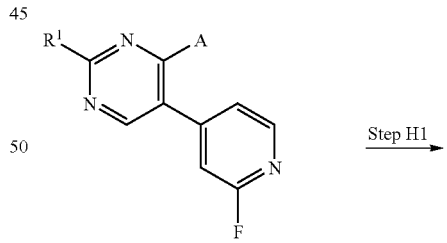

14

Step H1

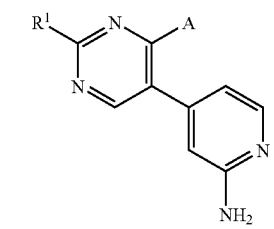

16 wherein A and $R^1$ have the same meanings as defined above. Compound (16) according to the present invention can be produced by allowing ammonia to act on Compound (14) which can be produced by Production Method C above to substitute the fluorine atom by an amino group (step H1). An ammonia gas saturated in a suitable solvent such as ethanol is used as the reagent in this reaction. In this reaction, it is preferable that the reaction solution is sealed in e.g. an autoclave and heated to about 150° C.

The starting compound in production of Compound (I) or (II) in the present invention may be in the form of a salt or a hydrate and is not particularly limited insofar as the reaction is not inhibited. Further, when Compound (I) or (II) in the invention is obtained in a free form, it can be converted in a usual manner into a salt form which Compound (I) or (III) may form. Further, the resultant isomers (for example, geometric isomer, optical isomer based on asymmetric carbon, stereoisomer, tautomer etc.) of Compound (I) or (II) of the present invention can be purified and isolated by usual separating means, for example recrystallization, diastereomer salt method, enzyme fractionation method, and various kinds of chromatography (for example, thin-layer chromatography, column chromatography, gas chromatography etc.).

Production Examples of the Pharmaceutical Composition or Compound of the Present Invention The pharmaceutical composition of the invention can be manufactured by a conventional method, and preferable preparation forms include tablets, powders, fine granules, granules, coated tablets, capsules, syrups, troches, inhalations, suppositories, injections, ointments, eye ointments, eye drops, nose drops, ear drops, poultices, lotions and the like. Ordinarily used fillers, binders, disintegrating agents, lubricants, coloring agents, flavoring agents, and as necessity, stabilizers, emulsifiers, absorption promoters, surfactants, pH adjusters, preservatives and antioxidants can be used in pharmaceutical manufacturing, and ingredients used generally as starting materials for pharmaceutical preparations can be blended in a usual manner for manufacturing. These ingredients include e.g. (1) animal and vegetable oils such as soybean oil, tallow and synthetic glyceride; (2) hydrocarbons such as liquid paraffin, squalane and solid paraffin; (3) ester oils such as octyldodecyl myristate and isopropyl myristate; (4) higher alcohols such as cetostearyl alcohol and behenyl alcohol; (5) silicon resin; (6) silicon oil; (7) surfactants such as polyoxyethylene fatty ester, sorbitan fatty ester, glycerin fatty ester, polyoxyethylene sorbitan fatty ester, polyoxyethylene hardened castor oil and polyoxyethylene polyoxypropylene block copolymer; (8) water-soluble polymers such as hydroethyl cellulose, polyacrylic acid, carboxyvinyl polymer, polyethylene glycol, polyvinyl pyrrolidone and methyl cellulose; (9) lower alcohols such as ethanol and isopropanol; (10) polyvalent alcohols such as glycerin, propylene glycol, dipropylene glycol and sorbitol; (11) sugars such as glucose and sucrose; (12) inorganic powder such as silicic anhydride, aluminum magnesium silicate and aluminum silicate; and (13) pure water.

1) The fillers include e.g. lactose, corn starch, white sugar, glucose, mannitol, sorbitol, crystalline cellulose, silicon dioxide etc.; 2) the binders include e.g. polyvinyl alcohol, polyvinyl ether, methyl cellulose, ethyl cellulose, arabic gum, tragacanth, gelatin, shellac, hydroxy propyl cellulose, hydroxy propylmethyl cellulose, polyvinyl pyrrolidone, polypropylene glycol-polyoxyethylene block polymer, meglumine, calcium citrate, dextrin, pectin etc.; 3) the disintegrating agents include e.g. starch, agar, gelatin powder, crystalline cellulose, calcium carbonate, sodium bicarbonate,.calcium citrate, dextrin, pectin, carboxymethyl cellulose calcium etc.; 4) the lubricants include e.g. magnesium stearate, talc, polyethylene glycol, silica, hardened vegetable oil etc.; 5) the coloring agents include e.g. those coloring agents approved to be added to pharmaceutical preparations; 6) the flavoring agents include cocoa powder, menthol, aromatic powder, peppermint oil, borneol, cinnamon powder etc.; and 7) the antioxidants include those approved to be added to pharmaceutical preparations, such as ascorbic acid and α-tocopherol.

1) The oral preparation is produced by mixing the active ingredient with fillers and if necessary with a binder, a disintegrating agent, a lubricant, a coloring agent, a flavoring agent etc., and then forming it in a usual manner into powders, fine granules, granules, tablets, coated tablets, capsules, etc. 2) The tablets and granules may be coated with a sugar or gelatin coating or if necessary with another suitable coating. 3) The liquid preparations such as syrups, injections and eye drops are prepared by mixing the active agent with a pH adjuster, a solubilizer and an isotonizing agent etc., and with a solubilizing aid, a stabilizer, a buffer, a suspension agent, an antioxidant etc. if necessary, followed by forming it into a preparation in a usual manner. The liquid preparation may be formed into a freeze-dried product and the injection can be administered intravenously, subcutaneously or intramuscularly. Preferable examples of the suspension agent include methyl cellulose, Polysorbate 80, hydroxyethyl cellulose, arabic gum, tragacanth powder, sodium carboxymethyl cellulose, polyoxyethylene sorbitan monolaurate etc.; preferable examples of the solubilizing aid include polyoxyethylene hardened castor oil, Polysorbate 80, nicotinamide, polyoxyethylene sorbitan monolaurate etc.; preferable examples of the stabilizer include sodium sulfite, sodium metasulfite, ether etc.; preferable examples of the preservative include methyl p-oxybenzoate, ethyl p-oxybenzoate, sorbic acid, phenol, cresol, chlorocresol etc. 4) The agent for external application can be produced in any conventional method. That is, the starting base material can make use of various starting materials ordinarily used in pharmaceutical preparations, non-pharmaceutical preparations, cosmetics, etc. For example, the material includes animal and vegetable oils, mineral oil, ester oil, waxes, higher alcohols, fatty acids, silicon oil, surfactants, phospholipids, alcohols, polyvalent alcohols, water-soluble polymers, clay minerals, pure water etc. If necessary, a pH adjuster, an antioxidant, a chelating agent, a preservative, a coloring agent, a perfume etc. can further be added. Further, ingredients having a differentiation-inducing action, a blood-stream promoting agent, a sterilizer, an antiinflammatory agent, a cell activator, vitamins, amino acids, a humectant, a keratin solubilizer etc. can also be incorporated as necessity.

Although the dose of the pharmaceutical composition or compound according to the present invention is varied depending on severity of symptoms, age, sex, body weight, administration form, type of salt, chemical sensitivity, specific type of disease etc., it is given daily in one portion or in divided portions into an adult in a dose of usually about 30 μg to 10 g, preferably 100 μg to 5 g, more preferably 100 μg to 100 mg for oral administration, or about 30 μg to 1 g, preferably 100 μg to 500 mg, more preferably 100 μg to 30 mg for injection.

Accordingly to this invention, there can be provided a novel pharmaceutical composition promoting defecation. The defecation-promoting agent according to the present invention is useful as a pharmaceutical preparation promoting physiological defecation. According to the present invention, there can also be provided a novel pyrimidine compound and a salt thereof. The compound or a salt thereof is useful as a pharmaceutical preparation exhibiting an excellent antagonistic action on adenosine $A_2$ receptor, particularly on $A_{2b}$ receptor, and simultaneously promoting defecation. Accordingly, the defecation-promoting pharmaceutical composition according to the present invention and the compound of the present invention are useful as an agent for treating, preventing or improving various kinds of constipation, for example functional constipation (acute constipation and various kinds of chronic constipation (for example, atonic constipation, spastic constipation, dyschezia, rectal constipation, chemically inducible constipation etc.)), organic constipation, enteroparalytic ileus, IBS, constipation accompanying IBS, constipation accompanying congenital digestive tract dysfunction, constipation accompanying ileus etc. Further, use of the defecation-promoting agent according to the present invention as a pharmaceutical preparation is not limited to the treatment, prevention or improvement of various kinds of constipation, but it is also useful as a chemical for evacuating intestinal tracts at the time of examination of digestive tracts or before and after an operation, as an aid for defecation after an operation, as a chemical for promotion of defecation after administering a contrast medium, and as a defecation-promoting agent when the patient is hypertensive or has a dangerous of cerebral apoplexy, cerebral infarction, cardiac infarction, etc.

EXAMPLES

As examples of the active ingredient in the pharmaceutical composition promoting defecation according to the present invention, the best mode except for the previously described known compounds is described. The previously described, known compounds and the following examples are described merely for illustrative purposes, and not intended to limit the compounds as the active ingredient in the pharmaceutical composition of the invention. Compounds not described specifically in the specification but having an $A_2$ receptor antagonism, particularly an $A_{2b}$ receptor antagonism and a salt thereof, are useful as the active ingredient in the defecation-promoting pharmaceutical composition according to the present invention, and such pharmaceutical compositions are included in the claims in this specification.

Reference Example 1

3-(3-Fluorophenyl)-2-(4-pyridyl)-2-propene nitrile

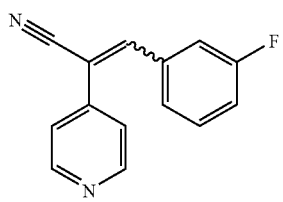

After sodium (3.0 g, 130 mmol) was dissolved in ethanol (150 mL), 4-pyridyl acetonitrile hydrochloride (33 g, 121 mmol) was added thereto and stirred at room temperature. After 10 minutes, 3-fluorobenzaldehyde (8 g, 65 mmol) was added thereto and stirred as such for 30 minutes. The resulting precipitates were collected by filtration and washed with a small amount of water, to give the title compound (8.2 g, 56%) as a colorless solid.

$^1$H NMR (400 MHz, DMSO-$d_6$) δ ppm; 7.40–7.46 (1H, m), 7.61–7.68 (1H, m), 7.75 (2H, dd, J=1.6, 4.4 Hz), 7.77–7.86 (2H, m), 8.37 (1H, s), 8.73 (2H, dd, J=1.6, 4.4 Hz).

Reference Example 2

1-(2-Furyl)-2-(4-pyridyl)-1-ethanone

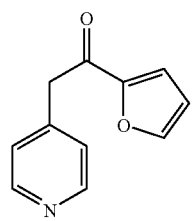

Lithium bis(trimethylsilyl)amide (100 mL, 100 mmol) was added dropwise over 1 hour to a solution of 4-picoline (4.6 g, 49.4 mmol) and ethyl 2-furancarboxylate (7.7 g, 54.9 mmol) in tetrahydrofuran (40 mL) at 0° C. in a nitrogen atmosphere, followed by stirring as such for 2 hours. Hexane (140 mL) was added to the reaction solution, and the resulting crystals were collected by filtration. The resulting crystals were dissolved in ethyl acetate and an aqueous saturated ammonium chloride solution. The organic layer was washed with an aqueous saturated ammonium chloride solution (×2) and brine, dried over anhydrous sodium sulfate, and concentrated. Hexane was added to the residue, and the resulting precipitates were collected by filtration and washed with hexane, to give the title compound (6.5 g, 70%) as a pale yellow solid.

$^1$H NMR (400 MHz, DMSO-$d_6$) δ ppm; 4.26 (2H, s), 6.77 (1H, dd, J=2.0, 3.6 Hz), 7.31 (2H, dd, J=1.6, 4.4 Hz), 7.65 (1H, dd, J=0.8, 3.6 Hz), 8.05 (1H, dd, J=0.8, 2.0 Hz), 8.51 (2H, dd, J=1.6, 4.4 Hz).

Reference Example 3

3-(Dimethylamino)-1-(2-furyl)-2-(4-pyridyl)-2-propene-1-one

N,N-dimethylformamide dimethyl acetal (5 mL) was added to 1-(2-furyl)-2-(4-pyridyl)-1-ethanone (2.0 g, 10.7 mmol) and stirred at 100° C. for 2 hours. After cooling as it was, the reacton mixture was diluted with ethyl acetate and an aqueous saturated ammonium chloride solution. The aqueous layer was extracted with ethyl acetate (×6). The combined organic layer was dried over anhydrous sodium sulfate and concentrated, to give the title compound (2.5 g, 97%) as a reddish brown oil.

$^1$H NMR (400 MHz, DMSO-d$_6$) δ ppm; 2.80 (6H, br s), 6.53 (1H, br), 6.60 (1H, br), 7.10 (2H, d, J=4.0 Hz), 7.65 (1H, br), 7.75 (1H, s), 8.44 (2H, d, J=4.0 Hz).

Example 1

6-(3-Flurophenyl)-5-(4-pyridyl)-2,4-pyrimidine diamine

After sodium (6.2 g, 268 mmol) was dissolved in ethanol (700 mL), 3-(3-fluorophenyl)-2-(4-pyridyl)-2-propene nitrile (50 g, 223 mmol) and guanidine hydrochloride (25.6 g, 268 mmol) were added thereto in this order and heated under reflux for 4 hours. After cooling as it was, the solvent was removed. Tetrahydrofuran (500 mL) was added to the residue, the insoluble matters were filtered off, and the filtrate was concentrated. A suspension of the residues and activated manganese dioxide (200 g) in chloroform (1000 mL) was heated under reflux for 2 hours. After cooling as it was, the manganese dioxide was filtered off through Celite, and washed with tetrahydrofuran (500 mL$^{33}$ 3) and methanol-chloroform (1:1) (1000 mL×2). The collected filtrate was concentrated, and then methanol was added to the residue. The resulting precipitates were collected by filtration, to give the title compound as a crude solid (14.6 g). The crude crystals were recrystallized from methanol-chloroform, to give the title compound (12.4 g, 20%) as a colorless solid.

$^1$H NMR (400 MHz, DMSO-d$_6$) δ ppm; 6.03 (2H, br s), 6.22 (2H, br s), 6.90–7.00 (2H, m), 7.01–7.12 (1H, m), 7.08 (2H, d, J=5.6 Hz), 7.16–7.23 (1H, m), 8.43 (2H, d, J=5.6 Hz); MS m/e (ESI) 282 (MH$^+$).

Example 2

6-(2-Furyl)-5-(4-pyridyl)-2,4-pyrimidinediamine

After sodium (3.2 g, 139 mmol) was dissolved in anhydrous ethanol (200 mL), 4-pyridyl acetonitrile hydrochloride (10.0 g, 64 mmol) and 2-furaldehyde (6.1 mL, 73.6 mmol) and guanidine hydrochloride (7.0 g, 73.3 mmol) were successively added thereto. After stirring at room temperature for 1 hour, it was heated under reflux for 7 hours. After cooling as it was, the insoluble matters were filtered off, washed with tetrahydrofuran, and the solvent was removed from the filtrate. Tetrahydrofuran (200 mL) and activated manganese dioxide (30.0 g) were added to the residue, followed by heating under reflux for 2.5 hours. After cooling as it was, the manganese dioxide was filtered through Celite, and washed with tetrahydrofuran. The collected filtrate was concentrated, and then methanol was added to the residues. The resulting precipitates were collected by filtration and washed with methanol, to give the title compound (3.48 g, 21%) as a pale brown solid.

$^1$H NMR (400 MHz, DMSO-d$_6$) δ ppm; 5.88 (2H, br s), 6.15 (2H, br s), 6.18 (1H, d, J=3.2 Hz), 6.38 (1H, dd, J=1.8, 3.2 Hz), 7.18 (2H, dd, J=1.4, 4.4 Hz), 7.47–7.51 (1H, m) 8.59 (2H, dd, J=1.4, 4.4 Hz).

Example 3

4-(2-Furyl)-5-(4-pyridyl)-2-pyrimidinyl amine

A suspension of 3-(dimethylamino)-1-(2-furyl)-2-(4-pyridyl)-2-propene-1-one (2.2 g, 9.08 mmol), guanidine hydrochloride (2.6 g, 27.2 mmol) and potassium carbonate (7.5 g, 54.3 mmol) in N,N-dimethylformamide (20 mL) was stirred at 70° C. for 12 hours. After cooling as it was, the reaction mixture was diluted with water. The resulting crystals were collected by filtration and washed with water, to give the title compound (1.73 g, 80%) as a pale yellow solid.

$^1$H NMR (400 MHz, DMSO-d,) δ ppm; 6.56 (1H, dd, J=1.6, 3.6 Hz), 6.68 (1H, dd, J=0.8, 3.6 Hz), 6.98 (2H, br s), 7.27 (2H, dd, J=1.6, 4.4 Hz), 7.67 (1H, dd, J=0.8, 1.6 Hz), 8.22 (1H, s), 8.56 (2H, dd, J=1.6, 4.4 Hz);

MS m/e (ESI) 239 (MH$^+$).

Example 4

4-(3-Fluorophenyl)-5-(4-pyridyl)-2-pyrimidinylamine

The title compound was synthesized in an identical or analogous method to that of Reference Example 2, Reference Example 3 and Example 3.

$^1$H NMR (400 MHz, DMSO-d$_6$) δ ppm; 7.04–7.07 (1H, m), 7.10 (2H, br s), 7.12–7.18 (1H, m), 7.14 (2H, dd, J=1.6, 4.4 Hz), 7.20–7.26 (1H, m), 7.32–7.38 (1H, m), 8.38 (1H, s), 8.45 (2H, dd, J=1.6, 4.4 Hz);

MS m/e (ESI) 267 (MH$^+$).

Example 5

4-Phenyl-5-(4-pyridyl)-2-pyrimidinylamine

The title compound was synthesized in an identical or analogous method to that of Reference Example 2, Reference Example 3 and Example 3.

$^1$H NMR (400 MHz, DMSO-d$_6$) δd ppm; 7.04 (2H, br s), 7.10 (2H, d, J=5.4 Hz), 7.28–7.41 (5H, m), 8.36 (1H, s), 8.42 (2H, d, J=5.4 Hz);

MS m/e (ESI) 249 (MH$^+$).

Example 6

5-(4-Pyridyl)-4-(2-thienyl)-2-pyrimidinylamine

The title compound was synthesized in an identical or analogous method to that of Reference Example 2, Reference Example 3 and Example 3.

$^1$H NMR (400 MHz, DMSO-d$_6$) δ ppm; 6.70 (1H, dd, J=1.2, 3.8 Hz), 6.94 (1H, dd, J=3.8, 5.2 Hz), 6.97 (2H, br s), 7.37 (2H, dd, J=1.6, 4.4 Hz), 7.67 (1H, dd, J=1.2, 5.2 Hz), 8.16 (1H, s), 8.61 (2H, dd, J=1.6, 4.4 Hz);

MS m/e (ESI) 255 (MH$^+$).

Example 7

4-(2-Pyridyl)-5-(4-pyridyl)-2-pyrimidinylamine

The title compound was synthesized in an identical or analogous method to that of Reference Example 2, Reference Example 3 and Example 3.

$^1$H NMR (400 MHz, DMSO-d$_6$) δ ppm; 7.02 (2H, dd, J=1.6, 4.6 Hz), 7.09(2H, br s), 7.37–7.41 (1H, m)), 7.71–7.75 (1H, m)), 7.88–7.93 (1H, m), 8.34–8.37 (1H, m), 8.37 (2H, dd, J=1.6, 4.6 Hz), 8.42 (1H, s);

MS m/e (ESI) 250 (MH$^+$).

Example 8

4-(3-Fluorophenyl)-5-(4-pyridyl)pyrimidine

The title compound was synthesized in an identical or analogous method to that of Reference Example 2, Reference Example 3 and Example 3.

$^1$H NMR (400 MHz, DMSO-$d_6$) δ ppm; 7.08–7.15 (2H, m), 7.17 (2H, dd, J=1.6, 4.4 Hz), 7.22–7.31 (2H, m)), 8.64 (2H, dd, J=1.6, 4.4 Hz), 8.77 (1H, s), 9.33 (1H, m);

MS m/e (ESI) 252 (MH$^+$).

Example 9

4-(3-Fluorophenyl)-5-(2-fluoro-4-pyridyl)pyrimidine

The title compound was synthesized in an identical or analogous method to that of Reference Example 2, Reference Example 3 and Example 3.

MS m/e (FAB) 270 (MH$^+$).

Example 10

4-(3-Fluorophenyl)-5-(2-fluoro-4-pyridyl)-2-pyrimidinyl amine

The title compound was synthesized in an identical or analogous method to that of Reference Example 2, Reference Example 3 and Example 3.

MS m/e (FAB) 285 (MH$^+$).

Example 11

N-[4-(3-Fluorophenyl)-5-(4-pyridyl)-2-pyrimidinyl]-N,N-dimethylamine

The title compound was synthesized in an identical or analogous method to that of Reference Example 2, Reference Example 3 and Example 3.

MS m/e (ESI) 295 (MH$^+$).

Example 12

N-[4, -(3-Fluorophenyl)-5-(4-pyridyl)-2-pyrimidinyl]-N-methylamine

The title compound was synthesized in an identical or analogous method to that of Reference Example 2, Reference Example 3 and Example 3.

MS m/e (ESI) 281 (MH$^+$).

Example 13

4-[4-(3-Fluorophenyl)-5-(4-pyridyl)-2-pyrimidinyl]morpholine

The title compound was synthesized in an identical or analogous method to that of Reference Example 2, Reference Example 3 and Example 3.

MS m/e (ESI) 337 (MH$^+$).

Example 14

N-[4-(3-Fluorophenyl)-5-(2-fluoro-4-pyridyl)-2-pyrimidinyl]-N-methylamine

The title compound was synthesized in an identical or analogous method to that of Reference Example 2, Reference Example 3 and Example 3.

MS m/e (FAB) 299 (MH$^+$).

Example 15

4-[4-(3-Fluorophenyl)-2-(methylamino)-5-pyrimidinyl]-1,2-dihydro-2-pyridinone A mixture of N-[4-(3-fluorophenyl)-5-(2-fluoro-4-pyridyl)-2-pyrimidinyl]-N-methylamine (30 mg, 0.101 mmol) and 6 N hydrochloric acid (3 mL) was heated under reflux for 40 minutes. The reaction solution was cooled as it was, and then washed with ethyl acetate. The aqueous layer was neutralized with 5 N aqueous sodium hydroxide, and then extracted with ethyl acetate, dried over anhydrous sodium sulfate and concentrated. The residue was suspended in diethyl ether, and then the resulting solid was collected by filtration and washed with diethyl ether, to give the title compound (20 mg, 67%)

MS m/e (FAB) 297 (MH$^+$).

Example 16

N-Ethyl-N-[4-(3-fluorophenyl)-5-(4-pyridyl)-2-pyrimidinyl]amine

The title compound was synthesized in an identical or analogous method to that of Reference Example 2, Reference Example 3 and Example 3.

MS m/e (FAB) 295 (MH$^+$).

Example 17

N1-[4-(3-Fluorophenyl)-5-(4-pyridyl)-2-pyrimidinyl]acetamide

A mixture of 4-(3-fluorophenyl)-5-(4-pyridyl)-2-pyrimidinylamine (200 mg, 0.751 mmol) acetic anhydride (6 mL) and conc. sulfuric acid (4 drops) was stirred at 90° C. for 16 hours. After cooling as it was, the reaction solution was diluted with ethyl acetate, water and a saturated aqueous sodium bicarbonate solution. The organic layer was washed with saturated sodium bicarbonate ($\times$2) and brine, and then dried over anhydrous sodium sulfate and concentrated. The residue was suspended in diethyl ether, and then the resulting solid was collected by filtration and washed with diethyl ether, to give the title compound (126 mg, 54%)

MS m/e (FAB) 309 (MH$^+$).

Example 18

N1-[4-(3-Fluorophenyl)-5-(4-pyridyl)-2-pyrimidinyl]-N1-methylacetamide

The title compound was synthesized in an identical or analogous method to that of Reference Example 2, Reference Example 3, Example 3 and Example 17.

MS m/e (FAB) 323 (MH$^+$).

Example 19

N1-[4-(3-Fluorophenyl)-5-(4-pyridyl)-2-pyrimidinyl]propanamide

The title compound was synthesized in an identical or analogous method to that of Reference Example 2, Reference Example 3, Example 3 and Example 17.
MS m/e (FAB) 323 (MH$^+$).

Example 20

N1-[4-(3-Fluorophenyl)-5-(4-pyridyl)-2-pyrimidinyl]butanamide

The title compound was synthesized in an identical or analogous method to that of Reference Example 2, Reference Example 3, Example 3 and Example 17.
MS m/e (FAB) 337 (MH$^+$).

Example 21

N1-[4-(3-Fluorophenyl)-5-(4-pyridyl)-2-pyrimidinyl]-N1-methylpropanamide

The title compound was synthesized in an identical or analogous method to that of Reference Example 2, Reference Example 3, Example 3 and Example 17.
MS m/e (FAB) 337 (MH$^+$).

Example 22

4-(3-Fluorophenyl)-5-(2-methyl-4-pyridyl)-2-pyrimidinylamine

The title compound was synthesized in an identical or analogous method to that of Reference Example 2, Reference Example 3 and Example 3.
MS m/e (FAB) 281 (MH$^+$).

Example 23

N1-Ethyl-N1-[4-(3-fluorophenyl)-5-(4-pyridyl)-2-pyrimidinyl]propanamide

The title compound was synthesized in an identical or analogous method to that of Reference Example 2, Reference Example 3, Example 3 and Example 17.
MS m/e (FAB) 351 (MH$^+$).

Example 24

N1-[4-(3-Fluorophenyl)-5-(2-fluoro-4-pyridyl)-2-pyrimidinyl]propanamide

The title compound was synthesized in an identical or analogous method to that of Reference Example 2, Reference Example 3, Example 3 and Example 17.
MS m/e (FAB) 341 (MH$^+$).

Example 25

N1-[4-(3-Fluorophenyl)-5-(2-methyl-4-pyridinyl)-2-pyrimidinyl]propanamide

The title compound was synthesized in an identical or analogous method to that of Reference Example 2, Reference Example 3, Example 3 and Example 17.
MS m/e (FAB) 337 (MH$^+$).

Example 26

4-[2-Amino-4-(3-fluorophenyl)-5-pyrimidinyl]-1,2-dihydro-2-pyridinone

The title compound was synthesized in an identical or analogous method to that of Reference Example 2, Reference Example 3, Example 3 and Example 15.
MS m/e (FAB) 283 (MH$^+$).

Example 27

N-Ethyl-N-[4-(3-fluorophenyl)-5-(2-fluoro-4-pyridyl)-2-pyrimidinyl]amine

The title compound was synthesized in an identical or analogous method to that of Reference Example 2, Reference Example 3 and Example 3.
MS m/e (FAB) 313 (MH$^+$).

Example 28

4-[2-(Ethylamino)-4-(3-fluorophenyl)-5-pyrimidinyl]-1,2-dihydro-2-pyridinone

The title compound was synthesized in an identical or analogous method to that of Reference Example 2, Reference Example 3, Example 3 and Example 15.
MS m/e (FAB) 311 (MH$^+$).

Example 29

N-[4-(3-Fluorophenyl)-5-(4-pyridyl)-2-pyrimidinyl]-N-propylamine

The title compound was synthesized in an identical or analogous method to that of Reference Example 2, Reference Example 3 and Example 3.
MS m/e (ESI) 309 (MH$^+$).

Example 30

N-[4-(3-Fluorophenyl)-5-(4-pyridyl)-2-pyrimidinyl]-N-phenylamine

The title compound was synthesized in an identical or analogous method to that of Reference Example 2, Reference Example 3 and Example 3.
MS m/e (ESI) 343 (MH$^+$).

Example 31

N-Ethyl-N-[4-(3-fluorophenyl)-5-(2-methyl-4-pyridyl)-2-pyrimidinyl]amine

The title compound was synthesized in an identical or analogous method to that of Reference Example 2, Reference Example 3 and Example 3.
MS m/e (ESI) 309 (MH$^+$).

Example 32

5-(2,6-Dimethyl-4-pyridyl)-4-(3-fluorophenyl)-2-pyrimidinylamine

The title compound was synthesized in an identical or analogous method to that of Reference Example 2, Reference Example 3 and Example 3.
MS m/e (ESI) 295 (MH$^+$).

Example 33

N-[5-(2,6-Dimethyl-4-pyridyl)-4-(3-fluorophenyl)-2-pyrimidinyl]-N-ethylamine

The title compound was synthesized in an identical or analogous method to that of Reference Example 2, Reference Example 3 and Example 3.
MS m/e (ESI) 323 (MH$^+$).

Example 34

4-(3-Fluorophenyl)-5-(3-methyl-4-pyridyl)-2-pyrimidinylamine

The title compound was synthesized in an identical or analogous method to that of Reference Example 2, Reference Example 3 and Example 3.
MS m/e (FAB) 281 (MH$^+$).

Example 35

5-(3-Ethyl-4-pyridyl)-4-(3-fluorophenyl)-2-pyrimidinylamine

The title compound was synthesized in an identical or analogous method to that of Reference Example 2, Reference Example 3 and Example 3.
MS m/e (FAB) 295 (MH$^+$).

Example 36

5-(2-Amino-4-pyridyl)-4-(3-fluorophenyl)-2-pyrimidinylamine

A mixture of 4-(3-fluorophenyl)-5-(2-fluoro-4-pyridyl)-2-pyrimidinylamine (100 mg, 0.352 mmol) and ammonia/ethanol (ethanol saturated with an ammonia gas under ice-cooling) (20 mL) was sealed in a test tube and stirred at 150° C. for 2 weeks. After cooling as it was, the reaction solution was concentrated. The residue was dissolved by adding ethyl acetate and water thereto. The organic layer was washed with water and brine, and then dried over anhydrous sodium sulfate and concentrated. The residue was purified by TLC plate (eluting solvent: dichloromethane/methanol=10/1), to give the title compound (12 mg, 12%).
MS m/e (FAB) 282 (MH$^+$).

Example 37

N4-Methyl-6-(3-fluorophenyl)-5-(4-pyridyl)-2,4-pyrimidinediamine

The title compound was synthesized in an identical or analogous method to that of Reference Example 2, Reference Example 3 and Example 3.
MS m/e (ESI) 296 (MH$^+$).

Example 38

N4, N4-Dimethyl-6-(3-fluorophenyl)-5-(4-pyridyl)-2,4-pyrimidinediamine

The title compound was synthesized in an identical or analogous method to that of Reference Example 2, Reference Example 3 and Example 3.
MS m/e (ESI) 310 (MH$^+$).

Example 39

N-Ethyl-N-[4-(2-furyl)-5-(4-pyridyl)-2-pyrimidinyl]amine

The title compound was synthesized in an identical or analogous method to that of Reference Example 2, Reference Example 3 and Example 3.
MS m/e (ESI) 267 (MH$^+$).

Example 40

N-Ethyl-N-[4-(3-fluorophenyl)-5-(4-pyridyl)-2-pyrimidinyl]amine

The title compound was synthesized in an identical or analogous method to that of Reference Example 2, Reference Example 3 and Example 3.
MS m/e (ESI) 310 (MH$^+$).

Example 41

N-Ethyl-N-[4-phenyl-5-(4-pyridyl)-2-pyrimidinyl]amine

The title compound was synthesized in an identical or analogous method to that of Reference Example 2, Reference Example 3 and Example 3.
MS m/e (ESI) 277 (MH$^+$).

Example 42

N-Ethyl-N-[5-(4-pyridyl)-4-(2-thienyl)-2-pyrimidinyl]amine

The title compound was synthesized in an identical or analogous method to that of Reference Example 2, Reference Example 3 and Example 3.
MS m/e (EST) 283 (MH$^+$).

Example 43

5-(3-Ethyl-4-pyridyl)-4-(2-furyl)-2-pyrimidinylamine

The title compound was synthesized in an identical or analogous method to that of Reference Example 2, Reference Example 3 and Example 3.
MS m/e (ESI) 267 (MH$^+$).

Example 44

N-Ethyl-N-[5-(3-ethyl-4-pyridyl)-4-(2-furyl)-2-pyrimidinyl]amine

The title compound was synthesized in an identical or analogous method to that of Reference Example 2, Reference Example 3 and Example 3.
MS m/e (ESI) 295 (MH$^+$).

Example 45

4-(2,5-Dimethyl-3-furyl)-5-(3-ethyl-4-pyridyl)-2-pyrimidinylamine

The title compound was synthesized in an identical or analogous method to that of Reference Example 2, Reference Example 3 and Example 3.
MS m/e (ESI) 267 (MH$^+$).

Example 46

N-[4-(2,5-Dimethyl-3-furyl)-5-(3-ethyl-4-pyridyl)-2-pyrimidinyl]-N-ethylamine

The title compound was synthesized in an identical or analogous method to that of Reference Example 2, Reference Example 3 and Example 3.
MS m/e (ESI) 295 (MH$^+$).

Example 47

5-(2,6-Dimethyl-4-pyridyl)-6-(3-fluorophenyl)-2,4-pyrimidinediamine

The title compound was synthesized in an identical or analogous method to that of Reference Example 2, Reference Example 3 and Example 3.
MS m/e (ESI) 310 (MH$^+$).

Example 48

4-(3-Methyl-2-furyl)-5-(4-pyridyl)-2-pyrimidinylamine

The title compound was synthesized in an identical or analogous method to that of Reference Example 2, Reference Example 3 and Example 3.
MS m/e (ESI) 253 (MH$^+$).

Example 49

N-[4-(3-Fluorpphenyl)-5-(4-pyridyl)-2-pyrimidinyl]methanesulfonamide

60% oily sodium hydride (20 mg, 0.500 mmol) was added to a solution of N1-[4-(3-fluorophenyl)-5-(4-pyridyl)-2-pyrimidinyl]acetamide (100 mg, 0.324 mmol) in tetrahydrofuran (10 mL) under ice-cooling in a nitrogen atmosphere. After stirring the reaction solution as it was for 20 minutes, methanesulfonyl chloride (30 μL, 0.388 mmol) was added dropwise thereto and stirred at room temperature. After 1 hour, 60% oily sodium hydride (20 mg, 0.500 mmol) and methanesulfonyl chloride (30 μL, 0.388 mmol) were additionally added thereto under ice-cooling, and further stirred at room temperature for 1 hour. The reaction solution was diluted with ethyl acetate and a saturated aqueous ammonium chloride solution. The organic layer was washed with a saturated aqueous ammonium chloride solution, a saturated aqueous sodium bicarbonate solution and a saturated aqueous ammonium chloride solution, and then dried over anhydrous sodium sulfate and concentrated. The residues were purified by TLC plate (eluting solvent: dichloromethane/methanol=10/1), to give a starting sulfonamide compound (70 mg). To the product were added tetrahydrofuran (10 mL) and 1 N hydrochloric acid (1 mL), followed by heating under reflux for 1 hour. After cooling as it was, the reaction solution was concentrated. The residue was suspended in diethyl ether, and then the resulting solid was collected by filtration and washed with diethyl ether, to give the title compound (68 mg, 55%) as hydrochloride.
MS m/e (ESI) 345 (MH$^+$).

Example 50

4,5-Di(4-pyridyl)-2-pyrimidinylamine

The title compound was synthesized in an identical or analogous method to that of Reference Example 2, Reference Example 3 and Example 3.
MS m/e (ESI) 250 (MH$^+$).

Example 51

4-(4-Methoxyphenyl)-5-(4-pyridyl)-2-pyrimidinylamine

The title compound was synthesized in an identical or analogous method to that of Reference Example 2, Reference Example 3 and Example 3.
MS m/e (ESI) 279 (MH$^+$).

Example 52

4-(3,4-Dimethoxyphenyl)-5-(4-pyridyl)-2-pyrimidinylamine

The title compound was synthesized in an identical or analogous method to that of Reference Example 2, Reference Example 3 and Example 3.
MS m/e (ESI) 309 (MH$^+$).

Example 53

4-[2-Amino-5-(4-pyridyl)-4-pyrimidinyl]phenol

The title compound was synthesized in an identical or analogous method to that of Reference Example 2, Reference Example 3 and Example 3.
MS m/e (ESI) 265 (MH$^+$).

Example 54

Methyl 3-[2-amino-5-(4-pyridyl)-4-pyrimidinyl]benzoate

The title compound was synthesized in an identical or analogous method to that of Reference Example 2, Reference Example 3 and Example 3.
MS m/e (ESI) 307 (MH$^+$).

Example 55

N4, N4-Dimethyl-6-(2-furyl)-5-(4-pyridyl)-2,4-pyrimidinediamine

The title compound was synthesized in an identical or analogous method to that of Reference Example 2, Reference Example 3 and Example 3.

MS m/e (ESI) 282 (MH$^+$)

TABLE 9

| Ex. No. | a | b | c | d |
|---|---|---|---|---|
| 1 | —NH$_2$ | 3-F—Ph | 4-Py | —NH$_2$ |
| 2 | —NH$_2$ | 2-Furyl | 4-Py | —NH$_2$ |
| 3 | —NH$_2$ | 2-Furyl | 4-Py | —H |
| 4 | —NH$_2$ | 3-F—Ph | 4-Py | —H |
| 5 | —NH$_2$ | Ph | 4-Py | —H |
| 6 | —NH$_2$ | 2-Thienyl | 4-Py | —H |
| 7 | —NH$_2$ | 2-Py | 4-Py | —H |
| 8 | —H | 3-F—Ph | 4-Py | —H |
| 9 | —H | 3-F—Ph | 2-F-4-Py | —H |
| 10 | —NH$_2$ | 3-F—Ph | 2-F-4-Py | —H |
| 11 | —NMe$_2$ | 3-F—Ph | 4-Py | —H |
| 12 | —NHMe | 3-F—Ph | 4-Py | —H |
| 13 | -(4-Morpholinyl) | 3-F—Ph | 4-Py | —H |
| 14 | —NHMe | 3-F—Ph | 2-F-4-Py | —H |
| 15 | —NHMe | 3-F—Ph | 1,2-2H-2-pyridinone-4-yl | —H |
| 16 | —NHEt | 3-F—Ph | 4-Py | —H |
| 17 | —NHCOMe | 3-F—Ph | 4-Py | —H |
| 18 | —N(Me)COMe | 3-F—Ph | 4-Py | —H |
| 19 | —NHCOEt | 3-F—Ph | 4-Py | —H |
| 20 | —NHCOn-Pr | 3-F—Ph | 4-Py | —H |
| 21 | —N(Me)COEt | 3-F—Ph | 4-Py | —H |
| 22 | —NH$_2$ | 3-F—Ph | 2-Me-4-Py | —H |
| 23 | —N(Et)COEt | 3-F—Ph | 4-Py | —H |
| 24 | —NHCOEt | 3-F—Ph | 2-F-4-Py | —H |
| 25 | —NHCOEt | 3-F—Ph | 2-Me-4-Py | —H |
| 26 | —NH$_2$ | 3-F—Ph | 1,2-2H-2-pyridinone-4-yl | —H |
| 27 | —NHEt | 3-F—Ph | 2-F-4-Py | —H |
| 28 | —NHEt | 3-F—Ph | 1,2-2H-2-pyridinone-4-yl | —H |
| 29 | —NHn-Pr | 3-F—Ph | 4-Py | —H |
| 30 | —NHPh | 3-F—Ph | 4-Py | —H |
| 31 | —NHEt | 3-F—Ph | 2-Me-4-Py | —H |
| 32 | —NH$_2$ | 3-F—Ph | 2,6-DiMe-4-Py | —H |
| 33 | —NHEt | 3-F—Ph | 2,6-DiMe-4-Py | —H |
| 34 | —NH$_2$ | 3-F—Ph | 3-Me-4-Py | —H |
| 35 | —NH$_2$ | 3-F—Ph | 3-Et-4-Py | —H |
| 36 | —NH$_2$ | 3-F—Ph | 2-NH$_2$-4-Py | —H |
| 37 | —NH$_2$ | 3-F—Ph | 4-Py | —NHMe |
| 38 | —NH$_2$ | 3-F—Ph | 4-Py | —NMe$_2$ |
| 39 | —NHEt | 2-Furyl | 4-Py | —H |
| 40 | —NHEt | 3-F—Ph | 4-Py | —H |
| 41 | —NHEt | Ph | 4-Py | —H |
| 42 | —NHEt | 2-Thienyl | 4-Py | —H |
| 43 | —NH$_2$ | 2-Furyl | 3-Et-4-Py | —H |
| 44 | —NHEt | 2-Furyl | 3-Et-4-Py | —H |
| 45 | —NH$_2$ | 2,5-Dimethyl-3-furyl | 3-Et-4-Py | —H |
| 46 | —NHEt | 2,5-Dimethyl-3-furyl | 3-Et-4-Py | —H |
| 47 | —NH$_2$ | 3-F—Ph | 2,6-DiMe-4-Py | —NH$_2$ |
| 48 | —NH$_2$ | 3-Methyl-2-furyl | 4-Py | —H |
| 49 | —NHSO$_2$Me | 3-F—Ph | 4-Py | —H |
| 50 | —NH$_2$ | 4-Py | 4-Py | —H |
| 51 | —NH$_2$ | 4-MeO—Ph | 4-Py | —H |
| 52 | —NH$_2$ | 3,4-DiMeO—Ph | 4-Py | —H |
| 53 | —NH$_2$ | 4-OH—Ph | 4-Py | —H |
| 54 | —NH$_2$ | 3-Methoxycarbonyl-Ph | 4-Py | —H |
| 55 | —NH$_2$ | 2-Furyl | 4-Py | —NMe$_2$ |

In the table above, Ph means a phenyl group; Py, pyridyl group; Me, methyl group; Et, ethyl group; DiMe, dimethyl group; n-Pr, n-propyl group; F, fluorine atom (fluoro); MeO, methoxy group; DiMeO, dimethoxy group; OH, hydroxyl group; and 2H, dihydro, resepectively.

Evaluation of Defecation-Promoting Action

The defecation-promoting action of the adenosine $A_{2b}$ receptor-inhibiting compound which was identified by measuring the binding ability and inhibitory ability thereof to the adenosine receptor in the above method, a salt thereof, a hydrate of them, or a pharmaceutical composition containing it can be evaluated on the basis of the method described in this specification.

That is, SD IGS rats (6-to 7-weeks-old, from Charles River) were placed in cages (3 animals/cage) and preliminarily allowed food and water ad libitum and raised for 1 week. On the day of the experiment, their weight was measured, a water-absorbing sheet was placed below each cage, and the animals were fasted but allowed water ad libitum throughout the experiment. Thee hours after fasting was initiated, the fecal pellets were recovered from each cage and observed for abnormality before the experiment, and then the compound suspended in 0.5% (w/v) methyl cellulose (MC) was orally administered in a dose of 5 ml/kg. On one hand, 0.5% (w/v) MC only was orally given to the control group. After administration of the compound, the rats were returned to the cage provided with a new water-absorbing sheet, and 180 minutes after the administration, the fecal pellets on the water-absorbing sheet were recovered from each cage, and the external appearance was observed, and the number of fecal pellets was counted. The number of fecal pellets is expressed per each cage.

Both compounds (I) and (II) in the invention exhibited an excellent adenosine $A_2$ receptor antagonism, and exhibited an excellent antagonism particularly to an adenosine $A_{2b}$ receptor. Further, both compounds (I) and (II) exhibited an excellent defecation-promoting action. The defecation-promoting action of the title compound in Example 1 is shown below. The defecation-promoting action of the title compound in Example 3 is as shown in the above tables.

TABLE 10

| Compound | Dose | The number of fecal pellets/3 rats | |
|---|---|---|---|
| Control | — | 4.67 ± 1.26 | |
| Example 1 | 3 mg/kg | 14.83 ± 1.82 | ** |
|  | 10 mg/kg | 23.17 ± 2.94 | *** |

The number of cages; n = 6 cages/group (18 rats/group)
p < 0.01, *p < 0.001, NS; not significant, Dunnett's test

The invention claimed is:
1. A compound represented by the formula:

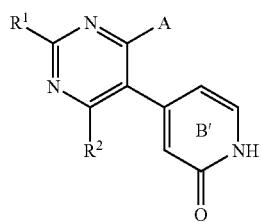

(II)

wherein

A represents a phenyl group, pyridyl group, thienyl group or furyl group which may be substituted with one or two groups selected from a halogen atom, a hydroxyl group, a $C_{1-6}$ alkyl group, a $C_{1-6}$ alkoxy group and a $C_{1-6}$ alkoxy-carbonyl group, $R^1$ represents a hydrogen atom, a morpholinyl group or a group represented by the formula —$NR^{1a}R^{1b}$, wherein $R^{1a}$ and $R^{1b}$ are the same as or different from each other and each represents a hydrogen atom, a $C_{1-6}$ alkyl group, a $C_{1-6}$ acyl group, a phenyl group or a $C_{1-6}$ alkylsulfonyl group, and $R^2$ represents a hydrogen atom or a group represented by the formula —$NR^{2a}R^{2b}$, wherein $R^{2a}$ and $R^{2b}$ are the same as or different from each other and each represents a hydrogen atom or a $C_{1-6}$ alkyl group; and B' may be substituted with one or more groups selected from a halogen atom, hydroxyl group, a $C_{1-6}$ alkyl group and amino group or a salt thereof.

2. A pharmaceutical composition comprising a pharmacologically effective amount of the compound according to claim 1, or a pharmacologically acceptable salt of thereof and a pharmaceutically acceptable carrier.

3. A method for promotion of defecation, by administering a pharmacologically effective amount of the compound described in claim 1 or a salt thereof to a patient.

4. A method for treating or improving constipation, by administering a pharmacologically effective amount of the compound described in claim 1 or a salt thereof to a patient.

5. The method according to claim 3, wherein the patient is suffering from a disease selected from the group consisting of constipation, functional constipation, spastic constipation, atonic constipation, irritable bowel syndrome, constipation accompanying irritable bowel syndrome, organic constipation, constipation accompanying enteroparalytic ileus, constipation accompanying congenital digestive tract dysfunction and constipation accompanying ileus, or combinations thereof.

6. The method according to claim 4, wherein the patient is suffering from a disease selected from the group consisting of constipation, functional constipation, spastic constipation, atonic constipation, irritable bowel syndrome, constipation accompanying irritable bowel syndrome, organic constipation, constipation accompanying enteroparalytic ileus, constipation accompanying congenital digestive tract dysfunction and constipation accompanying ileus, or combinations thereof.

* * * * *